(12) United States Patent
Kachroo et al.

(10) Patent No.: US 8,207,398 B2
(45) Date of Patent: Jun. 26, 2012

(54) PLANTS HAVING AN ENHANCED RESISTANCE TO NECROTROPHIC PATHOGENS AND METHOD OF MAKING SAME

(75) Inventors: Pradeep Kachroo, Lexington, KY (US); Aardra Kachroo, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/458,344

(22) Filed: Jul. 18, 2006

(65) Prior Publication Data

US 2007/0016978 A1    Jan. 18, 2007

Related U.S. Application Data

(60) Provisional application No. 60/700,212, filed on Jul. 18, 2005.

(51) Int. Cl.
*A01H 1/00* (2006.01)
*C12N 15/82* (2006.01)
*C12N 15/87* (2006.01)
*C07H 21/04* (2006.01)

(52) U.S. Cl. .................. 800/279; 800/278; 536/23.6

(58) Field of Classification Search .................. None
See application file for complete search history.

(56) References Cited

U.S. PATENT DOCUMENTS 6,103,520 A      8/2000  Topfer et al.
6,329,183 B1 *  12/2001  Skraly et al. ............ 435/135

FOREIGN PATENT DOCUMENTS

WO    WO 01/21820    *   3/2001

OTHER PUBLICATIONS

Manjunath et al. 1997, Plant Molecular Biology, 33:97-112.*
Kang et al. 2003 PNAS 100:3519-3524.*
Patton-Vogl et al. 2007, Biochemica et Biophysica Acta 1771:337-342.*
Kachroo et al. 2004, PNAS 101:5152-5157.*
Kang et al. 2003, PNAS, 100:3519-3524.*
Eastmond, P.J. (2004) Glycerol-insensitive *Arabidopsis* mutants: *gli1* seedlings lack glycerol kinase, accumulate glycerol and are more resistant to abiotic stress. Plant J. 37, 617-625.
Kachroo, A., Venugopal, S.C., Lapchyk, L., Falcone, D., Hildebrand, D. and Kachroo, P. (2004) Oleic acid levels regulated by glycerolipid metabolism modulate defense gene expression in *Arabidopsis*. Proc. Natl. Acad. Sci. USA. 101, 5152-5157.
Kachroo, P., Venugopal, S.C., Navarre, D.A., Lapchyk, L., Kachroo, A. (2005) Role of salicylic acid and fatty acid desaturation pathways in *ssi2*-mediated signaling. Plant Physiol. 139:1717-1735.
Kang, L., Li, J., Zhao, T., Xiao, F., Tang, X., Thilmony, R., He, S. and Zhou J.M. (2003) Interplay of the *Arabidopsis* nonhost resistance gene *NHO1* with bacterial virulence. Proc. Natl. Acad. Sci. USA 100, 3519-3524.
Nandi, A., Welti, R. and Shah, J. (2004) The *Arabidopsis thaliana* dihydroxyacetone phosphate reductase gene Suppressor of Fatty Acid Desaturase Deficiency1 is required for glycerolipid metabolism and for the activation of systemic acquired resistance. Plant Cell 16, 465-477.
Shen, W., Wei, Y., Dauk, M., Zheng, Z. and Zou, J. (2003) Identification of a mitochondrial glycerol-3-phosphate dehydrogenase from *Arabidopsis thaliana*: evidence for a mitochondrial glycerol-3-phosphate shuttle in plants. FEBS lett. 536, 92-96.
Wei, Y., Periappuram, C., Datla, R., Selvaraj, G. and Zou, J. (2001) Molecular and biochemical characterizations of a plastidic glycerol-3-phosphate dehydrogenase from *Arabidopsis*. Plant Physiol. Biochem. 39, 841-848.
Wei, Y., Shen, W., Dauk, M., Wang, F., Selvaraj, G. and Zou J. (2004) Targeted gene disruption of glycerol-3-phosphate dehydrogenase in *Colletotrichum gloeosporioides* reveals evidence that glycerol is a significant transferred nutrient from host plant to fungal pathogen. J. Biol. Chem. 279, 429-435; published online in advance of print Oct. 16, 2003.

* cited by examiner

*Primary Examiner* — Li Zheng

(74) *Attorney, Agent, or Firm* — Stites & Harbison PLLC; Mandy Wilson Decker

(57) ABSTRACT

A method for enhancing resistance to necrotrophic and/or hemibiotrophic pathogens by overexpressing glycerol-3-phosphate dehydrogenase using an expression vector in a plant species. For example, the present method can be used to enhance resistance to *C. higginsianum* by overexpressing glycerol-3-phosphate dehydrogenase in a plant such as *Arabidopsis* plant, using an expression vector in a plant.

10 Claims, 14 Drawing Sheets

Fig. 2(A)
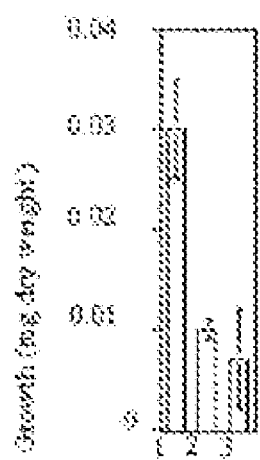
Fig. 2(B)
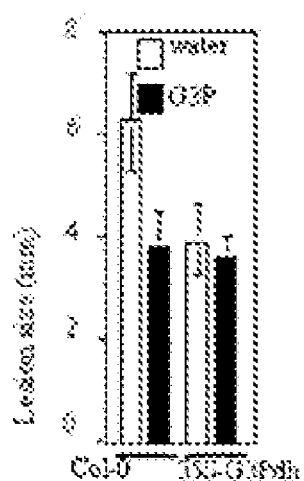
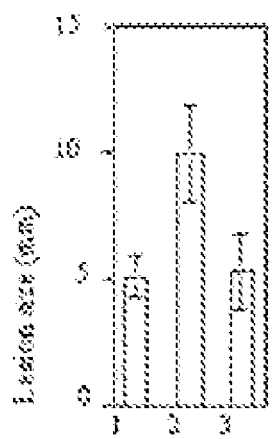
Fig. 2(C)
Fig. 2(D)

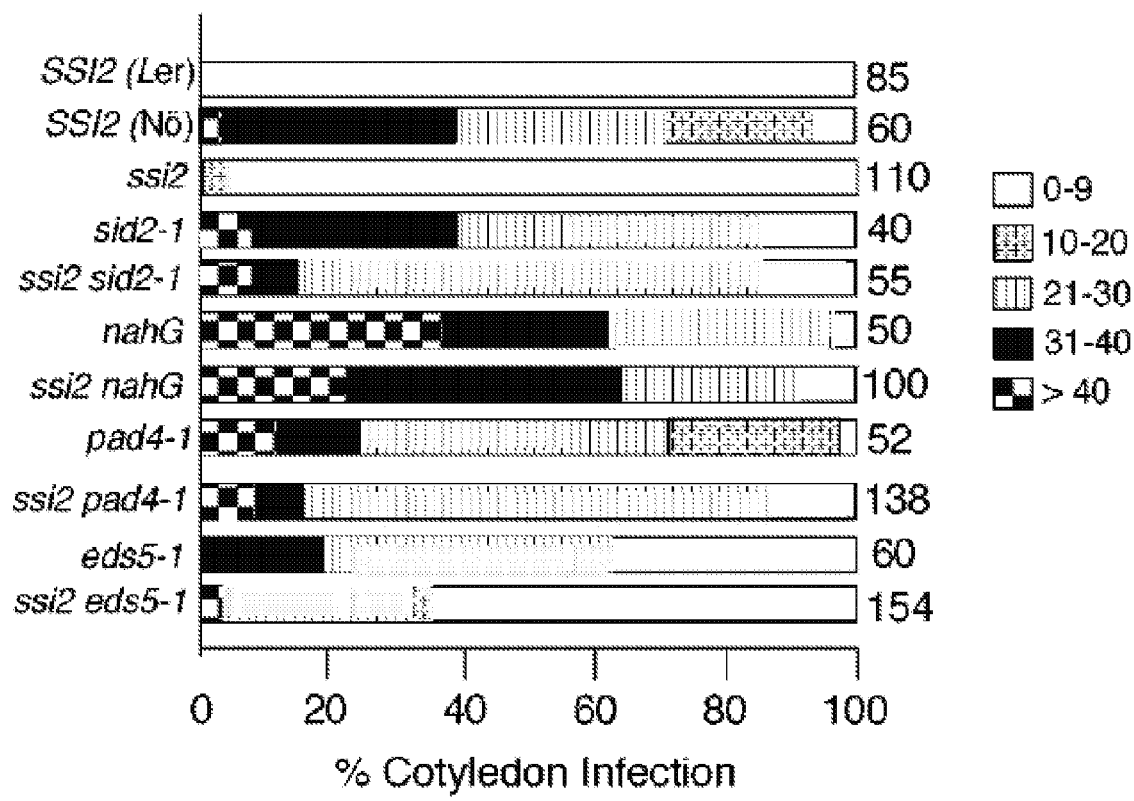

PLANTS HAVING AN ENHANCED RESISTANCE TO NECROTROPHIC PATHOGENS AND METHOD OF MAKING SAME

CROSS-REFERENCE TO RELATED APPLICATIONS

This application claims the benefit of provisional U.S. patent application No. 60/700,212, filed Jul. 18, 2005, herein incorporated in its entirety by reference.

FIELD OF THE INVENTION

The present invention relates to a method of conferring to plants an enhanced resistance to pathogens and plants having an enhanced resistance to pathogens.

BACKGROUND OF THE INVENTION

Plants have evolved various defense mechanisms to resist infection by pathogens. Upon recognition, the host plant initiates one or more signal transduction pathways that activate various plant defenses and thereby avert pathogen colonization. In many cases, resistance is associated with increased expression of defense genes, including the pathogenesis-related (PR) genes and the accumulation of salicylic acid (SA) in the inoculated leaf. The SA signal transduction pathway plays a pivotal role in plant defense signaling (see Durrant and Dong, 2004). When SA accumulation is suppressed in tobacco (*Nicotiana tabacum*) and *Arabidopsis* (*Arabidopsis thaliana*) by expression of the nahG transgene, which encodes the SA-degrading enzyme SA hydroxylase, susceptibility to both compatible and incompatible pathogens is enhanced and PR gene expression is suppressed (Gaffney et al., 1993; Delaney et al., 1994). Similarly, *Arabidopsis* mutants that are impaired in SA responsiveness, such as npr1 (Cao et al., 1997; Ryals et al., 1997; Shah et al., 1997), or pathogen-induced SA accumulation, such as eds1 (Falk et al., 1999), eds5 (Nawrath et al., 2002), sid2 (Wildermuth et al., 2001), and pad4 (Jirage et al., 1999), exhibit enhanced susceptibility to pathogen infection and impaired PR gene expression.

In addition to the major phytohormone-mediated defense pathways, fatty acid (FA)-derived signaling has also started to emerge as one of the important defense pathways (Vijayan et al., 1998; Kachroo et al., 2001, 2003b, 2004; Weber, 2002; Li et al., 2003; Yaeno et al., 2004). Desaturation of stearic acid (18:0)-acyl carrier protein (ACP) to oleic acid (18:1)-ACP catalyzed by the SSI2/FAB2-encoded stearoyl-ACP desaturase (S-ACP-DES) is one of the key steps in the FA biosynthesis pathway that regulates levels of unsaturated FAs in the cell (FIG. 9). A mutation in ssi2 confers stunted phenotype, constitutive PR gene expression, spontaneous lesion formation, and enhanced resistance to both bacterial and oomycete pathogens (Kachroo et al., 2001; Shah et al., 2001). By contrast, the ssi2 plants are unable to induce jasmonic acid (JA)-responsive gene PDF1.2 and show enhanced susceptibility to necrotrophic pathogen *Botrytis cinerea* (Kachroo et al., 2001, 2003b). The activity of the mutant S-ACP-DES enzyme was reduced 10-fold, resulting in elevation of 18:0 content in ssi2 plants (Kachroo et al., 2001). However, an increase in 18:0 does not contribute to altered defense signaling because several ssi2 suppressors show wild type-like signaling and yet accumulate high levels of 18:0 (Kachroo et al., 2003a).

A mutation in ssi2 also results in reduction in 18:1 content. The altered morphology and defense phenotypes in the ssi2 plants are restored by a loss-of-function mutation in the ACT1-encoded glycerol-3-P (G3P) acyltransferase, or in the GLY1-encoded G3P dehydrogenase (G3PDH), both of which elevate 18:1 levels in the ssi2 plants (Kachroo et al., 2003b, 2004). A mutation in gly1 and act1 results in reduced carbon flux through the prokaryotic pathway, which leads to a reduction in the hexadecatrienoic (16:3) acid levels (Kunst et al., 1988, Miquel et al., 1998). However, the gly1 and act1 plants continue to show normal growth characteristics, suggesting that increased flux through the eukaryotic pathway compensates for their defect. Because both 18:1 and G3P are required for the acyltransferase-catalyzed reaction, a reduction in either is likely to reduce the carbon flux through ACT1.

The levels of G3P and 18:1 can also be modulated by exogenous application of glycerol. The glycerol treatment leads to an increase in the endogenous G3P levels, which results in quenching of 18:1. Since the ACT1-catalyzed step is rate limiting, the quenching of 18:1 is more drastic in glycerol-treated ACT1-overexpressing lines (Kachroo et al., 2004). A reduction in the 18:1 in wild-type plants confers phenotypes similar to that of the ssi2 mutant.

G3P, an obligatory component for the biosynthesis of all plant glycerolipids, is generated either via the G3P dehydrogenase (G3PDH)-catalyzed reduction of dihydroxyacetone phosphate (DHAP) or via the glycerol kinase (GK)-catalyzed phosphorylation of glycerol. Plants contain several cytosolic, mitochondrial and plastidial isoforms of G3PDH (Shen et al., 2003; Wei et al., 2001) and all these may to contribute to the total G3P pool. Low levels of plastidial G3P due to a mutation in the GLY1-encoded G3PDH has been shown to reduce the carbon flux through the prokaryotic pathway. A mutation in gly1 leads to a reduction in the hexadecatrienoic (16:3) acid levels and this phenotype can be complemented by exogenous application of glycerol (Miquel et al. 1998; Miquel. 2003). The gly1-1 plants show normal growth characteristics, suggesting that contributions from the other G3PDH isoforms and increased flux through the eukaryotic pathway compensates for the defect in gly1. The GLY1-encoded G3PDH has recently been shown to participate in defense signaling in *Arabidopsis* (Kachroo et al, 2004; Nandi et al, 2004).

In comparison to G3PDH, only one GK has thus far been identified in *Arabidopsis*. The GLI1 (previously NHO1)-encoded GK has been shown to be required for non-host resistance against bacterial isolates of *Pseudomonas syringae* and resistance against the necrotrophic pathogen, *Botrytis cinerea* (Kang et al, 2003). The reasons why a defect in GK affects resistance to both bacterial and fungal pathogens have not been fully identified and described. Since gli1 plants are impaired in glycerol catabolism they accumulate glycerol, and these levels peak shortly after germination (Eastmond, 2004). The high level of glycerol in gli1 plants may increase the tolerance of the gli1 seedlings to various abiotic stress treatments including salt, freezing, desiccation and hydrogen peroxide (Eastmond, 2004).

Glycerol plays a role in various metabolic processes, including its conversion to glycerol-3-phosphate (G3P), which serves as a building block for glycerolipid biosynthesis. In plants, G3P is synthesized via the glycerol kinase-mediated phosphorylation of glycerol or via the G3P dehydrogenase (G3PDH)-mediated reduction of dihydroxyacetone phosphate. Both GK and G3PDH participate in host-pathogen interactions (Kang et al., 2003; Nandi et al., 2004; Kachroo et al., 2004).

Pathogens differ from saprophytes not only in their ability to recognize and penetrate host tissues, but also in the capability to access the nutrients available there. The establishment and maintenance of a metabolic sink by the pathogen is a crucial aspect of pathogenesis, but it has received very little attention in comparison to signaling related to initial recognition, and we do not understand much about it (Asahi et al., 1979; Pennypacker, 2000; Solomon et al., 2003; Oliver and Ipcho, 2004). Biotrophy is widely believed to differ from necrotrophy in this process (Mendgen and Hahn, 2002; Schulz-Lefert and Panstruga, 2003; Oliver and Ipcho, 2004). However, the molecular intractability of obligate biotrophs has made it difficult to test this hypothesis rigorously.

SUMMARY OF THE INVENTION

The present invention is directed to conferring pathogen resistance to various plant species. For example, the present method can confer enhancing resistance to necrotrophic and/or hemibiotrophic pathogens by overexpressing glycerol-3-phosphate dehydrogenase using an expression vector in a plant, such as Arabidopsis. The overexpression of glycerol-3-phosphate dehydrogenase can be achieved using an expression vector in a plant.

The present invention, in one form thereof, relates to a method for enhancing resistance to C. higginsianum by overexpressing glycerol-3-phosphate dehydrogenase in an Arabidopsis plant.

The present invention, in one another form thereof, relates to a method for enhancing resistance to C. higginsianum by overexpressing glycerol-3-phosphate dehydrogenase in a plant.

The present invention, in one another form thereof, relates to a method for enhancing the resistance to necrotrophic and/or hemibiotrophic pathogens by overexpressing glycerol-3-phosphate dehydrogenase using an expression vector in an Arabidopsis plant.

BRIEF DESCRIPTION OF THE DRAWINGS

FIG. 1(A) is an RNA blot comparison of glycerol-responsiveness in wild type (SSI2), act1, gli1, ssi2gly1-3 and 35S-ACT1 plants, FIG. 1(B) is a plot illustrating glycerol levels in wt (Col-0) and gli1 plants 72 hours after inoculations with water (white bar) or C. higginsianum spores (black bar), FIG. 1(C) is a plot of pathogen-induced changes in the 18:1 levels in leaf tissue of 4-week-old plants, where plants were treated with C. higginsianum, and samples taken 0, 12, 24, 72 and 94 hours after inoculation were analyzed for FAs using GC, FIG. 1(D) is a plot showing lesion size in wt (Col-0) and 35S-GLY1 plants, where the lesion size was determined 5 days post-inoculation (dpi) with C. higginsianum, FIG. 1(E) illustrates morphological phenotypes displayed by the mock (M) or C. higginsianum (C. h)-inoculated leaves from Col-0 and 35S-GLY1 plants at 5 dpi, FIG. 1(F) is a microscopy of trypan blue-stained leaves from Col-0 and 35S-GLY1 plants inoculated with C. higginsianum, where the profuse branching of mycelia in pathogen inoculated Col-0 leaf is indicated by a black arrow and the non-germinating spores on 35S-GLY1 leaf is indicated by a white arrowhead, and FIG. 1(G) is an RNA blot illustrating expression of the PR-1 gene in C. higginsianum inoculated plants 96 hours after spray inoculation.

FIGS. 2(A)-2(D) illustrate growth of C. higginsianum in liquid medium and anthracnose lesion development on Arabidopsis leaves where FIG. 2(A) is a plot for liquid cultures containing Fries minimal medium and 55 mM glycerol (gly, 1) or 10 mM glycerol-3-phosphate (G3P, 2) or both (3), were grown for 5 days on an orbital shaker at 30° C., FIG. 2(B) is a plot illustrating lesion size in wild type Col-0 and 35S-G3PDH transgenic plants infiltrated with water or G3P, FIG. 2(C) is a plot illustrating lesion size in wild type Col-0 (PAD3, 1), pad3 (2) and act1 pad3 (3) plants, and FIG. 2(D) illustrates morphological phenotypes displayed by the C. higginsianum-inoculated leaves from Col-0, gly1, gli1 and act1 plants at 5dpi.

FIG. 3(A) is a microscopy of trypan blue-stained leaves from indicated genotypes treated with water or 50 mM glycerol; FIG. 3(B) provides to plots for endogenous SA and SAG levels in the leaves of indicated 4-week-old soil-grown plants treated with water or glycerol; FIG. 3(C) is an RNA gel blot depicting expression of the PR-1 and PR-2 genes in indicated genotypes; FIG. 3(D) is a graph showing growth of P. parasitica biotype Emco5 on various plant genotypes; and FIG. 3(E) is a plot showing glycerol-induced changes In the 18:1 levels in leaf tissue of 4-week-old plants.

FIGS. 4(A)-4(E) illustrate morphological, molecular and biochemical phenotypes of wild type (wt), ssi2, ssi2 nahG, ssi2 sid2, ssi2 pad4, ssi2 eds1, ssi2 eds5 and ssi2 ndr1 plants where FIG. 4(A) comprises a series of photographs showing a comparison of the morphological phenotypes displayed by the wt, ssi2 and various double mutant plants in the ssi2 background; FIG. 4(B) is a microscopy of trypan blue-stained leaves from wt, ssi2 and various double mutant plants in the ssi2 background; FIG. 4(C) corresponds to endogenous SA and SAG levels in the leaves of indicated 4-week-old soil-grown plants treated with water or glycerol; FIG. 4(D) is a RNA gel blot for the expression of PR-1 and PR-2 genes; and FIG. 4(E) is a plot depicting growth of P. parasitica biotype Emco5 on various plant genotypes in accordance with the present invention.

FIG. 5(B) is an RNA gel blot showing the expression of the PR-1 gene in glycerol-treated fads, wt and act1 plants; FIG. 5(C) is a plot showing endogenous SA levels in the leaves of 4-week-old soil-grown wt (Col-O), fad3, fad5, fad7 and fad7 fadB plants treated with water (W) or glycerol; FIG. 5(D) is a plot showing glycerol-induced changes in the 18:1 levels in leaf tissue of four-week-old plants; FIG. 5(E) comprises a series of morphological phenotypes displayed by the ssi2 and various ssi2 fad double and triple mutants; FIG. 5(F) comprises a series of microscopies of trypan blue-stained leaves from ssi2 and various ssi2 fad double- and triple-mutants; FIG. 5(G) is an RNA gel blot for expression of PR-1 and PR-2 genes in wt, ssi2, and various ssi2 fad double and triple mutants; FIG. 5(H) comprises two plots showing endogenous SA and SAG levels in the leaves of 4-week-old soil grown 88/2, ssi2, ssi2 fad7 and ssi2 fad7 fadB plants; and FIG. 5(I) is an RNA gel blot depicting expression of the PDF1.2 gene in SSI2, ssi2, ssi2 fad7 and ssi2 fad7 fad8 plants.

FIG. 6(B) is a photograph showing a comparison of morphological phenotypes displayed by the 4-week-old soil-grown dgd1 and ssi2 dgd1 plants; FIG. 6(C) comprises three micrographs of trypan blue-stained leaves from ssi2, dgd1, and ssi2 dgd1 plants;

FIG. 6(D) is a RNA gel blot showing expression of the PR-1 gene in ssi2, dgd1 and ssi2 dgd1 plants.

FIG. 7(A) is a plot showing a profile of total lipids extracted from Col-0 and act1 plants treated with water or glycerol and FIG. 7(B) is a plot showing a comparison of total lipid content in water- and glycerol-treated Col-0 and act1 plants.

FIG. 8(A) is a plot showing glycerol-induced changes in the 18:1 levels in leaf tissue of 4-week-old plants; FIG. 8(B) is a plot depicting endogenous SA and SAG levels in the leaves of 4-week-old soil-grown plants; FIG. 8(C) is a photograph showing a comparison of morphological phenotypes displayed by a 16-day-old soil-grown ssi2 and various ssi2 gli1 plants; FIG. 8(D) comprises a series of micrographs for trypan blue-stained leaves from ssi2 and various ssi2 gli1 plants; and FIG. 8(E) is an RNA gel blot depicting expression of the PR-1 gene in ssi2 and ssi2 gli1 plants.

DETAILED DESCRIPTION

Figure 1A:
FIGS. 1(A)-1(G) illustrate glycerol levels and host response after glycerol or pathogen inoculations, where

The present invention is directed to conferring pathogen resistance to various plant species. For example, the present method can confer enhanced resistance to necrotrophic and/or hemibiotrophic pathogens by overexpressing glycerol-3-phosphate dehydrogenase using an expression vector in a plant, such as *Arabidopsis*. The overexpression of glycerol-3-phosphate dehydrogenase can be achieved using an appropriate expression vector in a plant.

The present invention is based on a newly discovered link between glycerol metabolism and ssi2-mediated defense signaling as reported in *Role of Salicylic Acid and Fatty Acid Desaturation Pathways in ssi2 Mediated Signaling*, Kachroo et al., 2005, Plant Physiology, herein incorporated by reference. The glycerol-mediated decline in 18:1 levels occurs in mutants that are impaired in the SA signaling pathway or affected in various FAD steps. The defense phenotypes associated with glycerol application are dependent on the ability of plants to utilize glycerol or acylate the glycerol-derived G3P with 18:1. Consistent with this result, a mutation in nho1 (gli1) renders plants tolerant to glycerol and unable to induce PR-1 gene expression in response to glycerol. ssi2-triggered phenotypes were not influenced by mutations that impair the SA pathway or that alter the levels of 16:3 or trienoic acids (16:3 and linolenic [18:3]). Since mutations in various FADs did not affect any of the ssi2 act1 phenotypes, it was concluded that complementation of the ssi2 mutation in the act1 background is not associated with the further conversion of 18:1 to linoleic acid (18:2) or 18:3 in plastidal or extraplastidal lipids.

The present invention relates to the use of exogenous glycerol to induce defense responses in plants, which implicates the importance of glycerol-mediated signaling. A novel discovered signaling pathway in *Arabidopsis* links fatty acid metabolism and defense, which provides evidence of an important aspect of signaling relevant to the establishment of this energy flow. Glycerol serves as an important building block for glycerolipid biosynthesis. Exogenous application of glycerol (at levels far below those that cause osmotic stress) induces SA-dependent defense responses in wild type *Arabidopsis* plants (Kachroo et al., 2004) (FIG. 1). However, *Arabidopsis* plants impaired in glycerol-3-phosphate (G3P) acyltransferase (ACT1) no longer respond to exogenous application of glycerol. The current hypothesis is that exogenous glycerol induces defense responses indirectly by causing an increase in G3P levels, which in turn depletes 18:1 content via ACT1.

Glycerol-3-phosphate dehydrogenase enzymes (G3PDH) play important roles in energy metabolism and biomass synthesis. A recent study reported that disruption of a G3PDH gene in *C. gloeosporioides* eliminated the ability of the mutant to grow on most carbon sources in vitro, including amino acids and glucose (Wei et al., 2004). However, it grew normally in the presence of glycerol. The mutant fungus also developed normally in its plant host (the round-leaved mallow), prompting the suggestion that glycerol, rather than glucose or sucrose, is the primary transferred source of carbon in plants. This was an unexpected finding, but direct analysis of infected host leaves revealed that their glycerol content did decrease by 40% within 48 hours of infection with *C. gloeosporioides* (Wei et al., 2004). Although this report should certainly be treated with some skepticism, given that growth in vitro may not resemble growth in vivo, it was found particularly intriguing because recent results have shown a link between glycerol metabolism and defense gene expression in *Arabidopsis* (Kachroo et al., 2004, 2005).

Figure 4A:
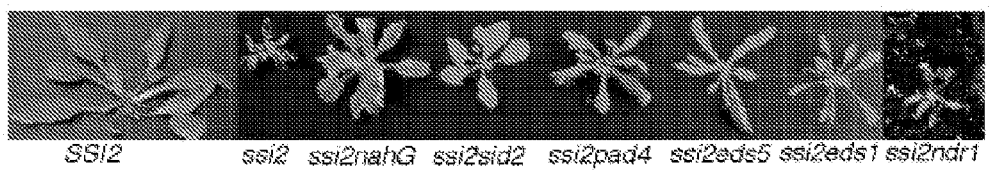

Treatment of *Arabidopsis* plants with glycerol activates defense gene expression. Several glycerol tolerant mutants have been characterized in an attempt to understand the mechanism of this activation. The act1 mutant, with a deficiency in glycerol-3-phosphate acyltransferase activity, is tolerant to exogenously applied glycerol. Furthermore, unlike the wild type, the expression of the PR-1 gene is not induced in the act1 mutant in response to glycerol (FIG. 4A; Kachroo et al., 2004). In collaboration with Deane Falcone's group at the University of Massachusetts, Lowell, the PI's group has characterized two additional glycerol tolerant mutants (gli12, gli22) which, like act1 plants, are tolerant to glycerol and do not express PR-1 upon exogenous application of glycerol. The gli1 (previously nho1) mutant, which is deficient in glycerol kinase (Kang et al., 2003), also shows tolerance to glycerol, accumulates high endogenous levels of glycerol (FIGS. 1(A) and 1(B)) and is hypersusceptible to the necrotroph *B. cinerea* (Kang et al., 2003). A link has been established between glycerol tolerance and reduced oleic acid (18:1) levels (Kachroo et al., 2003, 2004, 2005). Oleic acid levels have been strongly implicated as a signal for defense gene expression in studies of ssi2 mutants, which are deficient in production of 18:1, and constantly up-regulated in defense gene expression. More recently, a link is now established between oleic acid levels and SA-independent regulation of R gene. These results provide evidence that an intricate mechanism(s) involving glycerol underlies the regulation of oleic acid production and/or utilization.

Since the hemibiotroph *C. gloeosporioides* appears to be able to utilize glycerol for growth and conidiation in plants, evidence is provided which links glycerol metabolism and associated pathways in the host play an important role in establishment of infections by *Colletotrichum* fungi. Furthermore, since glycerol is involved in defense responses in the plant, it is possible that glycerol metabolism by the fungus acts to alter the native glycerol state and this serves as a signal for defense.

As a first step in determining the relationship between glycerol metabolism and disease resistance, it was determined that pathogen infection resulted in an decrease in the endogenous glycerol levels. This was determined using wild-type plants (Col-0) which were inoculated with *C. higgin-*

*sianum*, and the glycerol levels were measured 0, 1 and 3 days post-infection (dpi). The glycerol levels declined in a gradual manner after inoculation and were reduced by 50% at 3 dpi, in comparison to the water-treated controls (FIG. 1(B)). Wei et al. (2004) suggested that the decline in glycerol levels in inoculated round-leaved mallow leaves was due to pathogen uptake and utilization. Since untreated gli1 plants accumulate ~3-fold higher levels of glycerol as compared to wt plants (FIG. 1(B)), gli1 plants were insulated with *C. higginsianum* to determine whether higher levels of glycerol led to increased pathogen growth and enhanced susceptibility.

Figure 1B:
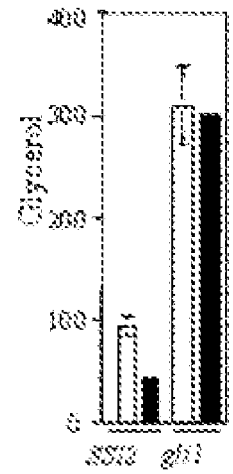

The mutant plants were consistently more susceptible than wild type plants (FIG. 2(D)), however their glycerol content was not reduced by pathogen inoculation (FIG. 1(B)). A plausible explanation accounting for utilization of glycerol in inoculated wt, but not in gli1 plants is that the pathogen itself is not utilizing significant amounts of glycerol, but that it is triggering the conversion of glycerol into G3P by the plant and that a defective glycerol kinase in gli1 is unable to utilize glycerol and generate G3P. An alternative possibility is that the gli1 mutation makes up for the pathogen utilized glycerol levels. To determine if glycerol can support the growth of fungus, *C. higginsianum* was cultured on medium containing glycerol as a sole source of carbon FIG. 2(A)). Interestingly, glycerol and glucose supported similar levels of growth, suggesting that the pathogen is quite capable of utilizing glycerol as a carbon source.

The decline in endogenous glycerol levels would be expected to result in an increase in G3P levels, if the plant itself is utilizing the glycerol. Because it has been difficult to accurately measure G3P directly, an indirect method was used to evaluate 18:1 levels in the presence and absence of the ACT1-catalyzed acylation reaction in water- and *C. higginsianum*-inoculated Col-0 and act1 plants. Reduction of 18:1 is correlated with increased G3P in wild type plants. In comparison to the water-sprayed plants, the pathogen-inoculated Col-0 showed ~2-fold reduction in their 18:1 content at 12 h after inoculation (FIG. 1(C)). The 18:1 levels remained low till 72 h after inoculation and were restored at 96 h after inoculation. By comparison, the pathogen inoculated act1 plants did not show any alteration in their 18:1 content, and presumably also maintained higher levels of G3P. The act1 plants were more resistant than the wild type plants (FIG. 2D). This provides evidence that *C. higginsianum* inoculation results in a plant-mediated increase in G3P levels, which depletes 18:1 levels via ACT1.

The GLY1 gene, a G3PDH, represents another route for G3P synthesis (FIGS. 1(A)-1(G)). The gly1 mutant was inoculated, which impacts the prokaryotic lipid pathway by lowering G3P levels. Similar to gli1, the gly1 mutant also showed slightly enhanced susceptibility to *C. higginsianum* (lesion size is ~12% larger, FIG. 2(D)). To ascertain if increased susceptibility in gly1 plants was in fact associated with the reduced G3P levels in these plants, the GLY1-encoded G3PDH was overexpressed in Col-0 plants (35S-GLY1). Two independent transgenic lines were analyzed and both lines showed markedly enhanced resistance to *C. higginsianum*; in comparison to Col-0, the 35S-GLY1 plants showed smaller and fewer lesions on spot- and spray-inoculated leaves, respectively (FIGS. 1(D) and 1(E)). Microscopic examinations of these lesions showed that pathogen inoculation on 35S-GLY1 caused hypersensitive-like cell death at the site of inoculation and was not associated with any mycelial proliferation (FIG. 1(F)). By comparison, Col-0 plants inoculated with *C. higginsianum* did not show any hypersensitive-like cell death and exhibited extensive proliferation of the pathogen (FIG. 1(F)). The spray-inoculated 35S-GLY1 plants showed ~3-fold lower PR-1 gene expression as compared to Col-0 plants (FIG. 1(G)), which further confirms that pathogen ingress in these plants was lower compared to Col-0 plants (induction of PR-1 by *C. higginsianum* is associated with susceptibility and necrotrophic growth of the fungus).

Taken together, these results provide evidence that accumulation of G3P and/or a G3P-derived metabolite play a key role in the interaction of *Arabidopsis* with *C. higginsianum*, especially during the early, biotrophic phase of the interaction when establishment of the infection court is taking place. Several lines of evidence point to G3P levels as being of primary importance. First, the act1 plants, which are likely to accumulate higher levels of G3P, showed slightly enhanced resistance towards *C. higginsianum* infection (this was further confirmed by mobilizing the act1 mutation in the pad3 background, FIG. 2(C)). Secondly, the gli1 and gly1 plants, with lower levels of G3P, are slightly more susceptible to *C. higginsianum*. Thirdly, overexpression of GLY1, expected to result in greatly elevated levels of G3P, showed pronounced resistance to *C. higginsianum*. Fourth, pharmacological and in vitro growth experiments showed that G3P inhibits *C. higginsianum*. When added in minimal medium containing a preferred carbon source like sucrose or glycerol, G3P inhibited fungal growth by ~3 fold (FIG. 2(A)). Furthermore, infiltration of G3P into *Arabidopsis* leaves, prior to infection, also significantly reduced necrosis triggered by the fungus at the site of entry (FIG. 2(B)).

As described herein, the present invention applies components of glycerol-mediated defense pathway and assess their impact on resistance to pathogens. It is shown that the glycerol-mediated decline in 18:1 levels occurs in mutants that are impaired in the R-gene, SA or fatty acid desaturation (fad) pathways. The defense phenotypes associated with glycerol application are dependent on the ability of plants to utilize glycerol or acylate the glycerol-derived G3P with 18:1. Pathogen inoculations of wt plants result in a decline in glycerol and 18:1 levels. It is shown that G3P levels play a role in defense and that overexpression of G3P dehydrogenase confers enhanced resistance to necrotrophic/hemibiotrophic pathogens.

The present invention is further illustrated by the following specific but non-limiting examples. The following examples are prophetic, notwithstanding the numerical values, results and/or data referred to and contained in the examples.

EXAMPLES

Methods
Plant Growth Conditions and Genetic Analysis

Plants are grown in the MTPS 144 Conviron (Winnipeg, MS, Canada) walk-in-chambers at 22° C., 65% relative humidity and 14 hour photoperiod. Mutations affecting the SA-signal transduction pathway are transferred in the ssi2 background by pollinating flowers of the ssi2 plants with pollen from npr1-5, eds1-2, pad4-1, eds5-1, ndr1-1, or sid2-1 plants. The ssi2 nahG transgenic plants used are described in more detail in Shah et al., 2001. Mutations affecting fatty acid desaturation (fad) or lipid biosynthesis are transferred in the ssi2 background by pollinating flowers of the ssi2 plants with pollen from fad3-1, fad4-1, fad5-1, fad6-1, fad7-2 and fad7-1 fad8-1. The ssi2 dgd1 and ssi2 gli1 plants are obtained by pollinating flowers of the ssi2 plant with pollen from dgd1-1 and gli1 plants, respectively. The ssi2 dgd1 act1 plants are obtained by pollinating flowers of the ssi2 dgd1 plant with pollen from ssi2 act1 plants.

The double and triple mutants are identified by cleaved amplified polymorphic sequence (CAPS) or derived-CAPS analyses, and by analyzing FA profiles. The genotypes at the ssi2 and act1 loci are determined as described in Kachroo et al., 2001 and Kachroo et al., 2003b. To distinguish FAD3 and GL/1 wt and mutant alleles, the fad3 and gli1 genes are sequenced and CAPS and dCAPS markers are developed, respectively.

Generation of Transgenic Plants Overexpressing GLY1

The GLY1 cDNA is amplified as a NcoII BamHI-linkered PCR product and cloned downstream of double 35S promoter in pRTL2.GUS vector. For *Arabidopsis* transformation the fragment containing promoter, GLY1 cDNA and terminator is removed from pRTL2-GLY1 vector and cloned into HindIII site of binary vectors pBAR1. The transgenic seeds containing pBAR1-derived vector are selected on soil sprayed with herbicide BASTA. The plants overexpressing high levels of GLY1 transgene are scored based on northern hybridizations and RT-PCR analyses.

RNA Extraction and Northern Analyses

Small-scale extraction of RNA from one or two leaves is performed in the TRIzol reagent (Invitrogen, Gaithersburg, Md.) following the manufacturer's instructions. Northern blot analysis and synthesis of random primed probes for PR-1, PR-2 and PDF1.2 are carried out as described in Kachroo et al., 2001.

Trypan Blue Staining

Leaf samples are taken from 2- or 4-week-old plants grown on soil. Trypan blue staining was performed as described in Bowling et al., 1997.

SA, FA and Lipid Analyses

SA and SA glucoside (SAG) are extracted and measured from 0.2-0.3 g of fresh weight leaf tissue, as described in Chandra-Shekara et al., 2004. FA analysis is carried out as described in Dahmer et al., 1989; and He et al., 2002. Lipids are extracted as described in Welti et al., 2002. Lipid profiles and acyl group identification are carried out using an automated electrospray ionization-tandem mass spectrometry facility available at the Kansas Lipidomics Center.

Glycerol and JA Treatments

Glycerol treatments are carried out by spraying 50 mM solution of glycerol prepared in sterile water. JA treatments are carried out as described in Kachroo et al., 2001.

Glycerol Estimation

Glycerol levels are determined using a glycerol kit (Roche-biopharm). The plant extracts are prepared from 1 gm of leaf tissue as described in Gerber et al., 1988. Briefly, the leaf tissues are homogenized in 5 ml of 0.1% phosphoric acid, filtered through cheesecloth, and the tissue extract collected after centrifugation at 15,000 g for 20 minutes was used for enzyme assays. Enzyme assays are carried out in three replicates.

Pathogen Infection

Inoculation with *Peronospora parasitica* Emco5 is conducted as described in Kachroo et al., 2001. Inoculation with *Colletotrichum higginsianum* is carried out by spraying the spores at a concentration of 105-106/ml and spot inoculating at a concentration of 104-105/ml. After inoculation, the plants are covered with a transparent plastic dome and kept in a growth chamber at 22° C., 65% relative humidity and 14 hour photoperiod. Infections are evaluated every day and scored for disease at 4-6 dpi. Inoculation with *Pseudomonas syringae* is conducted as described in Shah et al., 2001.

Results

Glycerol Induces SA Signaling via SID2—Dependent Pathway

Exogenous application of glycerol on wt plants lowers 18:1 levels and results in the induction of PR-1 gene expression (Kachroo et al., 2004). To determine the molecular components participating in this glycerol-mediated effect on the SA pathway, an experiment was conducted to test the response of eds1, eds5, pad4, ndr1, sid2, npr1 mutants and nahG transgenic plants to the exogenous application of glycerol with data summarized in Table 1.

TABLE 1

Fatty acid composition from leaf tissues of SS12, ssi2, eds1, ssi2 eds1, ndr1, ssi2 ndr1, eds5, ssi2 eds5, pad4, ssi2 pad4, sid2, ssi2 sid2, nahG, and ssi2 nahG plants. All measurements were made on 22° C. grown plants and data are described as mol % ± standard deviation calculated for a sample size of six.

| Genotype | 16:0 | 16:1 | 16:2 | 16:3 | 18:0 | 18:1 | 18:2 | 18:3 | Morphology |
|---|---|---|---|---|---|---|---|---|---|
| SS12 | 14.85 ± 1.41 | 4.10 ± 0.34 | 0.99 ± 0.33 | 16.30 ± 0.33 | 0.63 ± 0.08 | 2.31 ± 0.59 | 13.1 ± 1.55 | 47.72 ± 1.71 | Wt |
| ssi2 | 14.81 ± 2.10 | 2.86 ± 0.44 | 0.45 ± 0.18 | 9.0 ± 1.08 | 15.8 ± 2.82 | 0.6 ± 0.18 | 15.68 ± 1.72 | 40.8 ± 1.45 | Stunted |
| eds1 | 13.73 ± 0.41 | 4.66 ± 0.12 | 0.55 ± 0.04 | 17.95 ± 0.84 | 0.70 ± 0.04 | 1.27 ± 0.13 | 10.41 ± 0.64 | 50.73 ± 0.96 | Wt-like |
| ssi2 eds1 | 14.77 ± 2.75 | 3.85 ± 0.54 | 0.45 ± 0.1 | 10.18 ± 1.29 | 16.9 ± 1.89 | 0.8 ± 0.15 | 13.6 ± 2.39 | 39.25 ± 3.53 | ssi2-like |
| ndr1 | 14.6 ± 0.41 | 4.65 ± 0.12 | 1.01 ± 0.1 | 14.61 ± 0.67 | 0.54 ± 1.3 | 2.1 ± 0.48 | 13.87 ± 1.04 | 48.42 ± 0.98 | Wt-like |
| ssi2 ndr1 | 12.34 ± 0.33 | 2.0 ± 0.1 | 0.5 ± 0.1 | 9.84 ± 1.53 | 16.52 ± 1.3 | 0.70 ± 0.48 | 11.18 ± 1.04 | 45.30 ± 0.98 | ssi2-like |
| eds5 | 14.05 ± 0.36 | 4.29 ± 0.37 | 1.17 ± 0.14 | 16.39 ± 0.74 | 0.60 ± 0.06 | 2.39 ± 0.39 | 14.72 ± 1.05 | 46.39 ± 0.79 | Wt-like |
| ssi2 eds5 | 16.68 ± 2.31 | 3.85 ± 0.96 | 0.25 ± 0.04 | 8.88 ± 1.86 | 14.84 ± 2.59 | 0.94 ± 0.20 | 12.66 ± 0.65 | 41.84 ± 5.00 | ssi2-like |
| pad4 | 14.09 ± 0.88 | 4.09 ± 0.86 | 1.18 ± 0.22 | 15.91 ± 1.69 | 0.64 ± 0.11 | 2.27 ± 0.60 | 16.44 ± 2.29 | 46.38 ± 1.78 | Wt-like |
| ssi2 pad4 | 15.16 ± 0.48 | 3.05 ± 0.72 | 0.5 ± 0.1 | 8.62 ± 0.70 | 17.54 ± 2.36 | 0.88 ± 0.06 | 12.25 ± 0.73 | 42.00 ± 3.95 | ssi2-like |
| sid2 | 13.00 ± 0.36 | 4.23 ± 0.35 | 0.84 ± 0.19 | 17.24 ± 0.92 | 0.63 ± 0.06 | 1.42 ± 0.39 | 12.91 ± 1.90 | 49.73 ± 1.62 | Wt-like |
| ssi2 sid2 | 16.68 ± 1.51 | 5.1 ± 0.75 | 0.18 ± 0.02 | 10.66 ± 2.08 | 17.58 ± 1.80 | 0.68 ± 0.21 | 8.68 ± 0.62 | 40.42 ± 1.19 | ssi2-like |
| nahG | 14.68 ± 0.90 | 4.18 ± 0.68 | 1.14 ± 0.61 | 15.06 ± 2.30 | 1.19 ± 0.50 | 1.75 ± 0.92 | 14.27 ± 3.29 | 46.55 ± 3.47 | Wt-like |
| ssi2 nahG | 14.8 ± 2.63 | 3.32 ± 0.31 | 0.31 ± 0.08 | 10 ± 1.24 | 18.01 ± 1.07 | 0.9 ± 0.25 | 13.68 ± 0.91 | 39.18 ± 2.81 | ssi2-like |

Figure 3A:
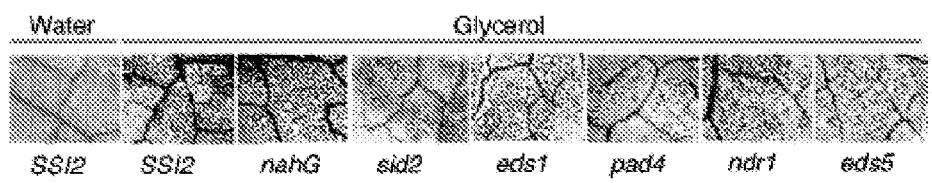
FIGS. 3(A)-3(E) illustrate glycerol-mediated effects on mutants impaired in SA or R-gene signaling where

The glycerol-and water-sprayed plants are evaluated for cell death, SA/SA glucoside (SAG) levels, PR expression, pathogen resistance and 18:1 levels. All genotypes show cell death on their leaves, suggesting that glycerol-induced cell death is independent o f mutations analyzed or the nahg transgene, as shown in FIG. 3(A), which is a microscopy of typan blue-stained leaves from indicated genotypes treated with water or 50 mM glycerol. Next, the levels of SA and SAG in water- and glycerol-treated plants are determined. Both Nossen (No) and Columbia-O (Col-O) plants show a 10- and 13-fold induction in SA levels and an 8- and 10-fold induction in the SAG levels, respectively (FIG. 3(B)). The SA/SAG levels in glycerol-treated eds1, eds5 and pad4 plants are higher compared to the water-treated plants but lower compared to the glycerol-treated wt plants. The sid2 plants show near basal levels of SA/SAG while ndr1 and npr1 plants accumulated higher than wt levels. These results indicate that SA levels generated upon glycerol treatment are partially dependent on EDS1, EDS5 and PAD4, and completely dependent on SID2. These results provide evidence that NDR1 and NPR1 negatively regulate the glycerol-triggered increase in SA/SAG levels.

Figure 3B:
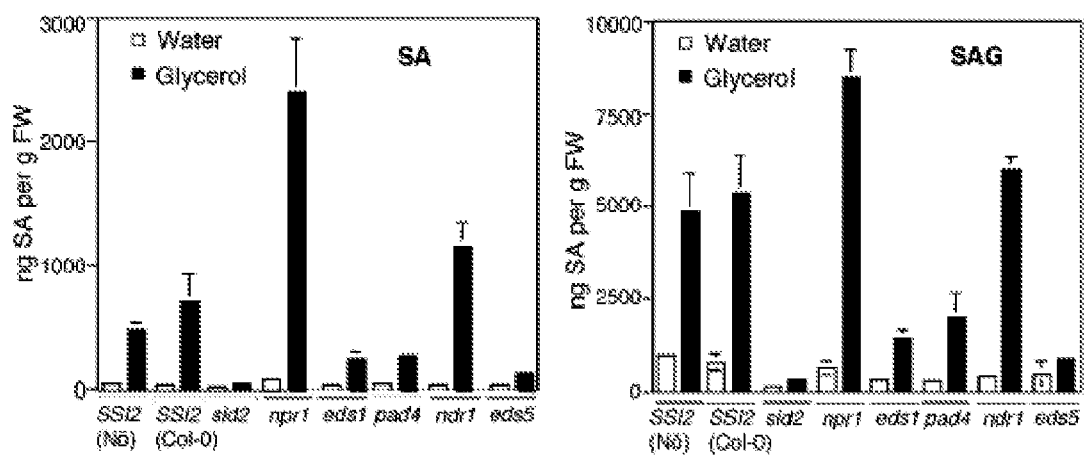
Figure 3C:
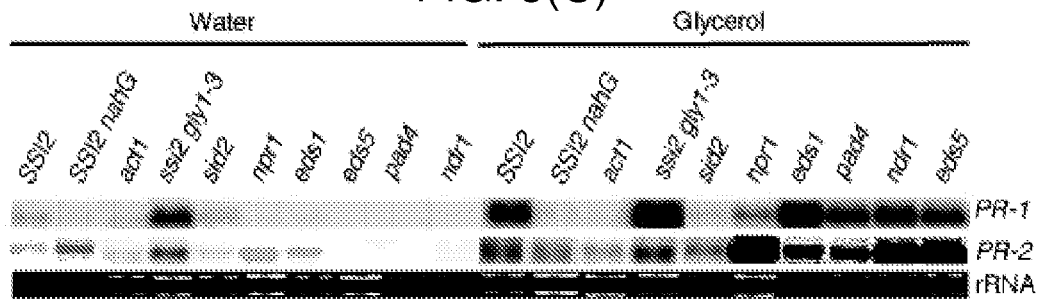

To determine if a correlation exists between glycerol-induced SA levels and PR gene expression, the expression of PR-1 and PR-2 genes in various genotypes treated with water or glycerol is evaluated (FIG. 3(C)). Although basal or low levels of PR-1 and PR-2, respectively, are seen in glycerol-treated sid2 and nahG plants, all the other mutant lines show induction of these transcripts upon glycerol treatment. The glycerol-treated ndr1, eds5, and npr1 plants induce higher levels of PR-2 gene as compared to the glycerol-treated wt plants. Taken together, these data provide evidence that glycerol-induced PR gene expression is dependent on the presence of a certain threshold level of SA/SAG, and these levels are derived via a SID2-dependent pathway.

Figure 3D:
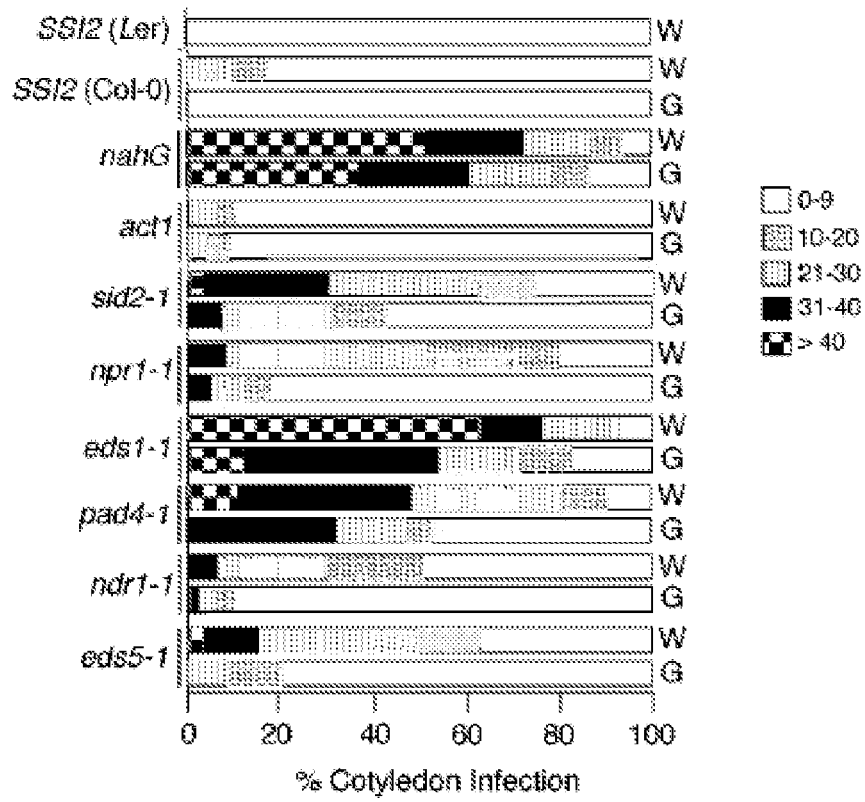
Figure 9:
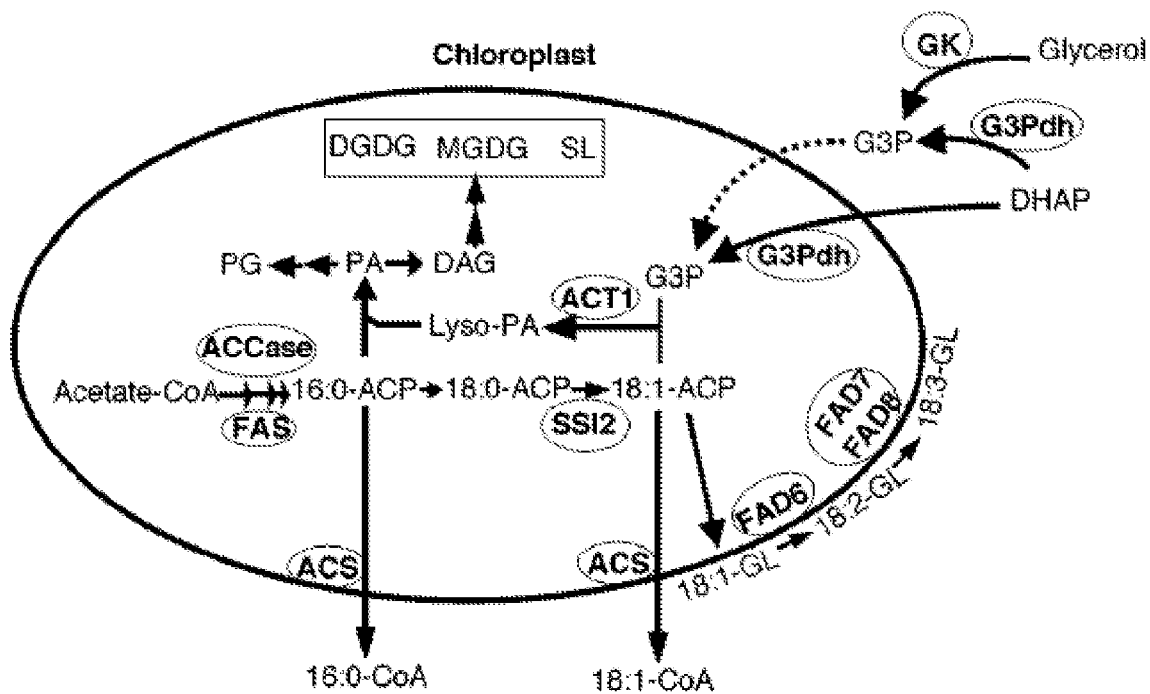
FIG. 9 is a schematic showing a condensed scheme for lipid biosynthesis and glycerol-mediated signaling in the *Arabidopsis* leaves.

The effect of mutations impairing the SA pathway on glycerol-induced resistance to Peronospora parasitica biotype Emco5 was also evaluated (FIG. 3(D)). Under the conditions tested, the wt Col-O plants showed susceptible resistance to Emc05, revealing less than 20% susceptibility. By comparison, the glycerol-treated Col-0 plants are as tolerant as the resistant ecotype Landsberg (Ler). The water-treated eds1, eds5, pad4, sid2, ndr1, npr1and nahG plants show susceptibility to Emco5. Glycerol treatment has a little or no effect on the nahG plants. A partial enhancement in resistance is observed in glycerol-treated pad4, eds5, ndr1 and sid2 plants. A more pronounced effect is observed in glycerol-treated npr1 plants, which show about 60% reduction in the number of susceptible plants. The glycerol-treated eds1 plants show only a marginal, 10% reduction in the number of susceptible plants. Taken together, these data provide evidence that glycerol-mediated resistance to Emco5requires the functions of EDS1, PAD4, EDS5, SID2and NDR1. Similar to Col-0 plants, only about 10% of water-treated act1plants display susceptibility. Consistent with the glycerol-insensitive phenotype of act1plants, glycerol treatment of act1does not enhance resistance to Emco5 (FIG. 9).

To establish a correlation between the glycerol induced phenotypes and 18:1 levels, the leaf 18:1 content is determined three days after glycerol application. Both wt and plants impaired in the SA signaling pathway show a drastic reduction in their 18:1 levels after glycerol application (FIG. 3(E)), and these are comparable to 18:1 levels in ssi2 plants. By comparison, act1 plants, which are unable-to acyl ate 18:1, do not show a decrease in their 18:1 levels.

Figure 4B:
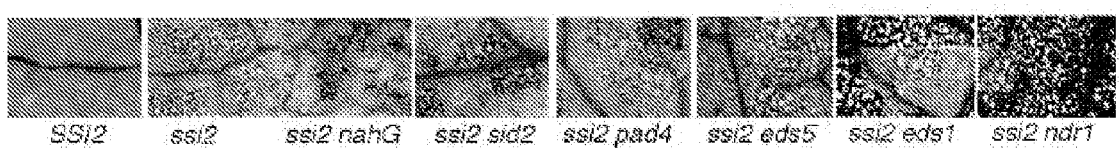
Figure 4C:
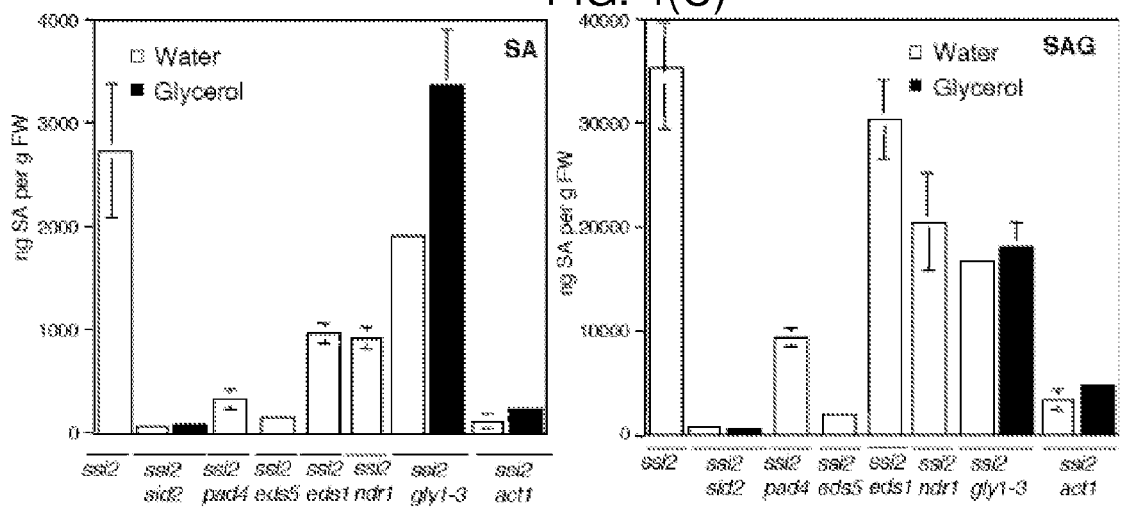
Figure 4D:
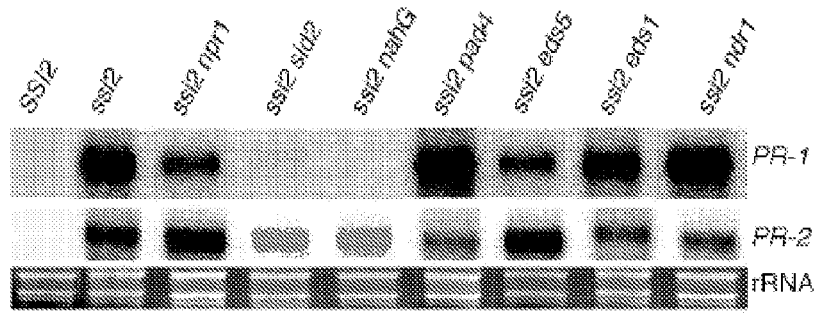

SA Signaling Mutants Affect the SA Levels but do not Restore Altered Defense Signaling in ssi2 Plants Prior data has suggested that glycerol application on wt plants converts these into ssi2-mimics by lowering their 18:1 levels (Kachroo et al., 2004). To determine if the glycerol effect seen on single mutants defective in SA or R-gene signaling pathways is similar to the effects exerted by these mutations on ssi2-triggered phenotypes, ssi2 double mutant plants in eds1, pad4, eds5, ndr1 and sid2 backgrounds are constructed. All the double mutant plants show hypersensitive response-like lesions on their leaves and except ssi2 ndr1 all other double mutant and ssi2 nahG plants are slightly bigger than the ssi2 plants (FIGS. 4(A) and 4(B)). In comparison to ssi2 plants, ssi2 eds 1, ssi2 pad4 and ssi2 eds5 accumulat low levels, and ssi2 sid2 plants show basal levels, of SA and SAG (FIG. 4(C)). These results provide evidence that the high levels of SA in ssi2 plants partially contribute to their stunted phenotype but not their cell death phenotype. Thus, EDS1, PAD4, EDS5 and SID2 appear to contribute to the SA levels in ssi2 plants and the SA/SAG in ssi2 plants is possibly derived via a SID2-dependent pathway. This possibility is further supported when exogenous application of glycerol is able to upregulate the SA/SAG levels in ssi2 gly1-3 plants, but not in ssi2 sid2 and ssi2 act1 plants (FIG. 4(C)).

Consistent with the reduced levels of SA, PR-1 gene expression decreases to basal levels in ssi2 sid2 and ssi2 nahG plants (FIGS. 4(A)-4(E)). A moderate reduction in PR-1 levels is also observed in ssi2 npr1 and ssi2 eds5 plants, while ssi2 eds1, ssi2 pad4 and ssi2 ndr1 plants show levels similar to those in ssi2 plants. As seen in glycerol-treated single mutant plants, the expression of PR-2 is upregulated by mutations in npr1 and eds5 and an increased basal level expression is also seen in ssi2 sid2 and ssi2 nahG plants.

These results indicate that high levels of PR expression in ssi2 plants can be triggered by the presence of a certain threshold of SA/SAG (FIGS. 4(A)-4(E)). To determine if any correlation exists between SA levels/ PR-gene expression and pathogen resistance, the response of ssi2 pad4, ssi2 eds5, ssi2 sid2 and ssi2 nahG plants to the virulent pathogen Emco5 is tested (FIG. 4(E)). Similar to the resistance spectrum seen in glycerol-treated single mutants (FIG. 4(E)), a mutation in pad4, eds5 or sid2 increases the susceptibility of ssi2 plants to Emco5. Since ssi2 eds1-2 plants are in the RPP8 background (McDowell et al., 1998), which confers resistance to Emco5, these plants are inoculated with a virulent bacterial pathogen *Pseudomonas syringae*. The eds1-2 mutation compromises the enhanced bacterical resistance conferred by the ssi2 mutation (data not shown; Shah et al., 2001). A higher degree of susceptibility seen in ssi2 pad4 and ssi2 eds1 as compared to ssi2 eds5 plants further suggests that ssi2-conferred resistance does not correlate with either the levels of SA, or the expression of PR-1.

Various ssi2-containing genotypes are analyzed for their FA levels to determine if a correlation exists between 18:1 levels and phenotypes exhibited by these plants (See Table 1). All double mutant and ssi2 nahG plants show increased levels of 18:0 and a decrease in the 18:1 content, which is consistent with the presence of the ssi2 mutation in these plants. A moderate decrease in the 16:3 levels is also noticed in all plants containing the ssi2 mutation. Taken together, these results show that phenotypes seen in glycerol-treated plants defective in the SA pathway are similar to the respective double mutant plants.

Glycerol Application or Presence of the ssi2 Mutation in fad Mutants Produce Similar Effects To examine the role of the FA desaturation pathway in the induction of glycerol-mediated ssi2-like phenotypes, mutants affected in various steps of fatty acid desaturation (fad) are treated with glycerol (Table 1). The fad2, fad3, fad4, fad5, fad6, fad7, and fad7 fad8 plants show visible and microscopic cell death lesions on their leaves upon exposure to glycerol (FIG. 5(A)). However, the extent of lesion formation is maximal in fad5 plants and least in fad7 and fad7 fad8 plants (FIG. 5(A)). These morphological and microscopic phenotypes also correlate with the PR-1 gene expression as well as SA levels; PR-1 expression and SA levels are highest in glycerol-treated fad5 plants and lowest in glycerol-treated fad7 or fad7 fad8 plants (FIGS. 5(B) and 5(C)). Although glycerol treatment induces higher expression of PR-1 in fad3 plants, their morphological phenotype is not as pronounced as that of fad5 plants. The SA levels after glycerol treatment are highest in fad5 plants followed by fad3 and wt plants. Although the fad7 and fad7 fad8 plants show increases in SA levels upon glycerol treatment, these levels are 3-fold lower than those in wt plants. Fatty acid profiling of water- and glycerol-treated fad2, fad3, fad4, fad5 and fad6 plants show a glycerol-triggered decline in 18:1 to levels comparable to those seen in the ssi2 plants (FIG. 5(D) and data not shown). By comparison, the glycerol-treated fad7 and fad7 fad8 plants show only a moderate reduction in 18:1 and these levels are higher than those in the ssi2 plants. As expected, while the ssi2 act1 plants does not alter their JA responsiveness and, like ssi2, these plants continue to show basal level expression of PDF1.2 upon exogenous application of JA (FIG. 5(I)). The ssi2 fad5, ssi2 fad4, and ssi2 fad5 plants are also non-responsive to JA (data not shown). Fatty acid profiling of ssi2 fad5, ssi2 fad4 and ssi2 fad5 plants show these contained 18:1 levels comparable to those seen in the ssi2 plants (as provided in Table 2).

TABLE 2

Fatty acid composition from leaf tissues of SS12, ssi2, fad2, fad3, ssi2 fad3, fad4, ssi2 fad4, fad5, ssi2 fad5, fad6, ssi2 fad6, fad7, ssi2 fad7, fad7 fad8, ssi2 fad7 fad8 plants. All measurements were made on 22° C. grown plants and data are described as mol % ± standard deviation calculated for a sample size of six.

| Genotype | 16:0 | 16:1 | 16:2 | 16:3 | 18:0 | 18:1 | 18:2 | 18:3 | Morphology |
|---|---|---|---|---|---|---|---|---|---|
| SS12 | 18.1 ± 0.47 | 4.5 ± 0.46 | 0.5 ± 0.35 | 16.02 ± 0.77 | 0.88 ± 0.10 | 2.2 ± 0.07 | 12.52 ± 2.86 | 47.38 ± 2.24 | Wt |
| ssi2 | 14.12 ± 1.10 | 3.01 ± 0.65 | 0.45 ± 0.10 | 4.4 ± 1.23 | 15.1 ± 2.22 | 0.7 ± 0.10 | 13.33 ± 2.12 | 42.54 ± 2.47 | Stunted |
| fad2 | 13.7 ± 1.10 | 4.47 ± 0.42 | 1.58 ± 0.31 | 20.58 ± 0.72 | 0.42 ± 0.13 | 14.55 ± 2.47 | 4.18 ± 0.35 | 40.42 ± 1.43 | Wt-like |
| $$ | 17.33 ± 1.33 | 2.66 ± 0.40 | 0.33 ± 0.08 | 7.32 ± 1.52 | 10.83 ± 0.54 | 10.54 ± 2.02 | 3.84 ± 0.40 | 37.85 ± 1.52 | ssi2-like |
| fad3 | 14.59 ± 0.66 | 4.22 ± 0.32 | 1.44 ± 0.27 | 16.4 ± 0.58 | 0.8 ± 0.12 | 3.42 ± 0.57 | 18.84 ± 1.73 | 33.5 ± 2.25 | Wt-like |
| ssi2 fad3 | 12.58 ± 1.80 | 3.55 ± 0.28 | 0.4 ± 0.1 | 10.52 ± 2.71 | 14.72 ± 2.14 | 1 ± 0.41 | 20.3 ± 4.18 | 38.52 ± 5.0 | ssi2-like |
| fad4 | 17.83 ± 0.38 | 0.7 ± 0.07 | 1.18 ± 0.15 | 16.22 ± 0.31 | 0.8 ± 0 | 2.28 ± 0.35 | 13.00 ± 1.43 | 48.04 ± 1.99 | Wt-like |
| ssi2 fad4 | 21.08 ± 1.34 | — | — | 8.84 ± 0.38 | 8.82 ± 1.40 | 0.0 ± 0.1 | 10.78 ± 1.08 | 47.04 ± 2.01 | ssi2-like |
| fad5 | 25.54 ± 0.63 | 4.04 ± 0.81 | — | — | 1.3 ± 0.1 | 2.5 ± 0.38 | 14.7 ± 1.84 | 52.18 ± 1.38 | Wt-like |
| ssi2 fad5 | 20.22 ± 1.65 | 1.88 ± 0.14 | 0.4 ± 0.1 | — | 81.88 ± 2.02 | 1.1 ± 0.22 | 12.44 ± 0.43 | 42.3 ± 1.67 | ssi2-like |
| fad6 | 14.52 ± 0.58 | 17.35 ± 1.30 | — | — | 8.88 ± 0.10 | 22.72 ± 0.38 | 13.45 ± 0.07 | 31.57 ± 0.85 | Wt-like |
| ssi2 fad6 | 17.5 ± 0.62 | 8.3 ± 0.55 | — | — | 11.35 ± 0.05 | 11.58 ± 0.87 | 18.4 ± 0.92 | 34.75 ± 1.75 | Larger than ssi2 |
| fad7 | 13.42 ± 0.88 | 4.5 ± 0.45 | 10.0 ± 0.35 | 4.1 ± 0.04 | 0.54 ± 0.15 | 3.54 ± 0.21 | 31.2 ± 1.94 | 31.14 ± 1.50 | Wt-like |
| ssi2 fad7 | 10.22 ± 1.38 | 4.27 ± 0.55 | 11.8 ± 0.8 | 2.55 ± 0.5 | 15.47 ± 2.03 | 1.0 ± 0.42 | 24.88 ± 1.29 | 20.39 ± 1.40 | Lager than ssi2 |
| fad7 fad8 | 12.88 ± 0.34 | 5.35 ± 0.18 | 15.24 ± 0.78 | — | 0.53 ± 0.04 | 3.35 ± 0.53 | 33.73 ± 0.97 | 3.42 ± 1.22 | Wt-like |
| ssi2 fad7 fad8 | 14.88 ± 1.43 | 4.65 ± 0.80 | 14.81 ± 0.28 | 0.51 ± 0.5 | 14.33 ± 2.61 | 2.05 ± 0.25 | 36.9 ± 1.48 | 12.11 ± 1.74 | Larger than ssi2 | do not show any drop in 18:1 levels, ssi2 gly-3 plants show a drastic decline. Taken together, these results imply a positive correlation between reduction in 18:1 levels and the appearance of glycerol-induced phenotypes in fad mutants.

In order to further test the hypothesis that the glycerol sensitivity of fad5 is related to the ssi2-associated defense, ssi2 fad5, ssi2 fad4, ssi2 fad5, ssi2 fad7 double mutant and ssi2 fad7 fad8 triple mutant plants are generated. The morphological and biochemical characteristics of ssi2 fad2 and ssi2 fad6 plants have been described in Kachroo et al., 2003b. The morphological phenotypes in ssi2 fad3 and ssi2 fad4 are similar to that of ssi2 (FIG. 5(E)). Interestingly, ssi2 fad5 shows a more stunted and chlorotic phenotype, and ssi2 fad7 is slightly less stunted than ssi2 plants. The ssi2 fad7 and ssi2 fad7 fad8 plants display normal leaf morphology during initial stages of growth, but develop lesions on their leaves after two weeks of growth (FIG. 5(F)). The ssi2 fad3, ssi2 fad4 and ssi2 fad5 plants all develop lesions and show microscopic cell death. The morphological phenotype also correlates with expression of PR-1 in these plants; all the ssi2 fad plants show high level expression of the PR-1 gene (FIG. 5(G)). By contrast, the ssi2-triggered PR-2 gene expression is drastically reduced in ssi2 fad7 and ssi2 fad7 fad8 plants, but remains high in other ssi2 fad plants. Analysis of SA/SAG levels in ssi2 fad7 and ssi2 fad7 fad8 plants show that these genotypes contain lower levels of SA/SAG as compared to ssi2 (FIG. 5(H)). However, the levels of SA and particularly those of SAG in ssi2 fad7 and ssi2 fad7 fad8 plants were higher than those in wt plants. This suggests that fad7 and fad8 mutations have a partial effect on the ssi2-triggered phenotypes. A decrease in the SA/SAG levels in ssi2 fad7 and ssi2 fad7 fadB By comparison, the 18:1 levels in ssi2 fad7 and ssi2 fad7 fad 8 plants are higher than those in ssi2 and lower compared to the wt plants. These results suggest that ssi2 phenotypes are independent of FAD5, FAD4 and FAD5 genes and partially dependent on FAD7 and FAD7 FAD8 genes.

Phosphatidic Acid (PA) or PA-Derived Downstream Signaling is not Associated with the Glycerol- or ssi2-Triggered Phenotypes The act1 mutation restores all the ssi2-triggered defense phenotypes because it increases the 18:1 levels in these plants. Since the ACT1-catalyzed reaction eventually leads to the biosynthesis of PA, it is possible that the reduced levels of PA in ssi2 act1 plants contribute to restoration of mutant phenotypes. This is plausible since PA levels are known to be induced during host-pathogen interactions (De Jong et al., 2004) and PA is likely to have a role in signaling (Zhang et al., 2003). To test the role of PA in ssi2-triggered defense phenotypes a lipid profile of ssi2 plants was generated. The levels of PA in ssi2 plants are similar to those in wt plants (FIG. 6(A)), suggesting that high levels of PA are not responsible for ssi2 phenotypes. Since glycerol application to wt plants induces an ssi2-like phenotype, PA levels in water- and glycerol-treated wt and act1 plants were measured. The PA levels in act1 plants are about 2.8-fold lower than the wt plants, and these levels do not change significantly after glycerol application. By comparison, the glycerol-treated wt plants show a marginal reduction in PA levels. These results suggest that glycerol application impacts the ACT1-mediated acylation step without increasing PA levels.

PA produced in the prokaryotic pathway is converted to diacylglycerol, which then serves as a precursor for synthesis of monogalactosyldiacylglycerol (MGDG) and digalactosyldiacylglycerol (DGDG). To understand the role of these components in ssi2-triggered signaling, ssi2 dgd1 double mutant plants are generated, which double mutant plants are impaired in the synthesis of DGDG. The ssi2 dgd1 double mutant plants show rosette leaf arrangement like that of dgd1 plants but are smaller than dgd1 plants and show visible and microscopic cell death lesions on their leaves (FIGS. 6(B) and 6(C)). The double mutant plants contain low levels of 18:1 and accumulate high levels of PR-1 (Table 3, FIGS. 6(A)-6(D)).

is not further altered upon glycerol treatment. These results suggest that glycerol application possibly slows down the growth rate of the plants, similar to that observed in the ssi2 plants.

Inability to Metabolise Glycerol Abolishes the Glycerol-Induced Responses

To determine the specificity of the glycerol-mediated induction of defense responses, and to define other components of glycerol-triggered defense pathway, a mutant line is analyzed which is impaired in glycerol catabolism due to a mutation in the gene encoding GK (GLI1, Kang et al., 2003).

TABLE 3

Fatty acid composition from leaf tissues of SS12, ssi2, gli1, dgd1 and ssi2 dgd1 plants. All measurements were made on 22° C. grown plants and data are described as mol % ± standard deviation calculated for a sample size of six.

| Genotype | 16:0 | 16:1 | 16:2 | 16:3 | 18:0 | 18:1 | 18:2 | 18:3 | Morphology |
|---|---|---|---|---|---|---|---|---|---|
| SS12 | 16.16 ± 0.5 | 4.24 ± 0.29 | 1.24 ± 0.08 | 16.44 ± 0.38 | 0.92 ± 0.32 | 2.58 ± 0.06 | 13.44 ± 0.77 | 44.98 ± 0.89 | Wt |
| ssi2 | 14.62 ± 2.13 | 3.12 ± 0.59 | 0.52 ± 0.18 | 10.55 ± 0.89 | 12.97 ± 2.71 | 0.95 ± 0.21 | 12.32 ± 2.23 | 44.95 ± 2.96 | Stunted |
| gli1 | 15.58 ± 0.45 | 4.04 ± 0.23 | 1.06 ± 0.06 | 16.48 ± 0.25 | 0.76 ± 0.11 | 2.56 ± 0.28 | 13.06 ± 0.89 | 46.44 ± 1.40 | Wt-like |
| ssi2 gli1 | 17.1 ± 1.66 | 2.79 ± 0.6 | 0.18 ± 0.16 | 10.2 ± 1.1 | 13.8 ± 2.4 | 0.85 ± .10 | 9.78 ± 0.45 | 45.26 ± 2.59 | ssi2-like |
| dgd1 | 24.47 ± 0.91 | 4.6 ± 0.74 | 0.4 ± 0.1 | 3.2 ± 0.21 | 1.15 ± 0.1 | 1.41 ± 0.27 | 7.3 ± 0.53 | 57.47 ± 1.6 | Smaller than wt |
| ssi2 dgd1 | 80.25 ± 2.27 | 2.16 ± 0.88 | 0.44 ± 0.11 | 4.54 ± 0.96 | 12.66 ± 1.53 | 1 ± 0.10 | 11.4 ± 0.63 | 47.55 ± 2.28 | ssi2-like |

These results are further corroborated by glycerol application to dgd1 plants; as in wt plants, glycerol treatment of dgd1 plants causes a decline in 18:1 levels and induces high level expression of PR-1 (data not shown). Together, these results suggest that a mutation in dgd1 is not sufficient to restore ssi2 phenotypes. Furthermore, the ssi2-triggered phenotypes in dgd1 plants are restored by the act1 mutation, as judged by the lack of cell death lesions on their leaves (data not shown).

Glycerol Application Lowers Total Lipid Content in Wild Type Plants

Figure 7A:
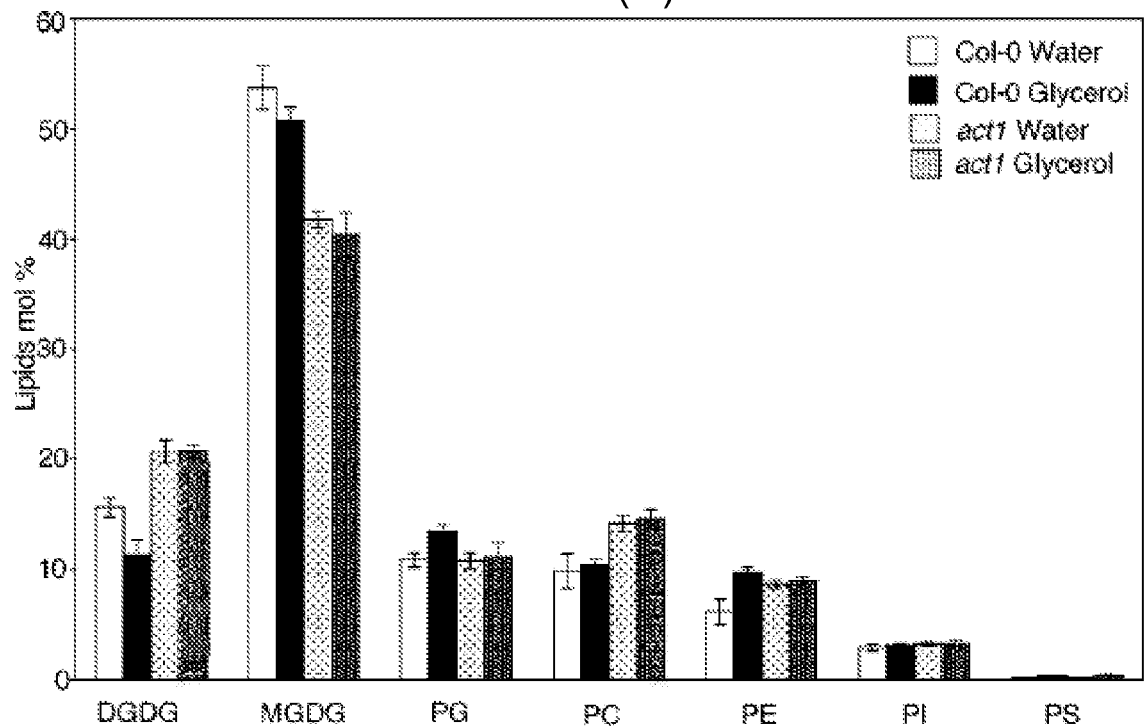
FIGS. 7(A) and 7(B) depict the lipid profile and total lipid content where

In order to determine if the glycerol-mediated induction of cell death and defense gene expression in wt plants is associated with an altered lipid profile, the levels of individual lipids and the levels of total acyl carbons on each of these lipids are measured. The lipid profiles are obtained for both leaf and chloroplasts of wt and act1 plants and compared with those of ssi2 plants. Glycerol application results in a decline in the levels of leaf MGDG and DGDG in the wt plants and a marginal increase in the levels of phosphotidylglycerol (PG) and phosphatidylethanolamine (PE). By comparison, act1 plants do not show any significant alteration in the levels of MGDG, DGDG, PG and PE (FIG. 7(A)). The chloroplastic lipid profile of wt plants match the profile obtained from whole leaves (data not shown). The levels of total acyl carbons and the total double bonds on each individual lipid do not alter significantly between glycerol- and water-treated samples (FIGS. 3(A)-3(E)). These results provide evidence that glycerol application does not alter the levels of plastidal and/or extraplastidal lipids or the number of acyl carbon groups on the individual lipids.

Figure 7B:
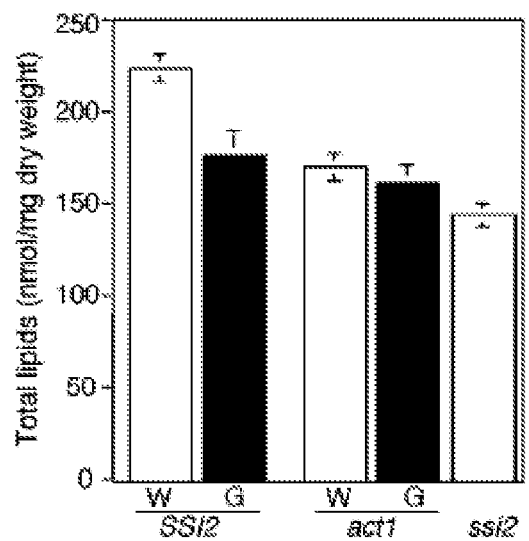

Following-up on the observation that the ssi2 plants show a significant reduction in total lipid content in comparison to the wt plants (FIG. 7(B)), total lipid content in glycerol- and water-treated wt plants are determined. Interestingly, the wt plants show a statistically significant decline in the total nmoles of lipids per mg dry weight (223 versus 164) upon glycerol application (FIG. 7(B)). Although the total lipid content of act1 plants is significantly lower than wt plants, it As seen in the act1 plants, the gli1 plants do not show any reduction in the 18:1 levels upon glycerol treatment (FIG. 8(A)). By comparison, wt, ssi2 gly1-3 and ACT1-overexpressing (35S-ACT1) plants show a reduction in 18:1 (FIG. 8(A)). A glycerol-mediated decline in 18:1 levels also correlates with the amount of SA and SAG accumulated in these plants and the levels of PR-1 gene expression. Upon glycerol treatment, the highest levels of SA and PR-1 gene expression are seen in 35S-ACT1 plants, followed by wt plants (FIGS. 8(B) and 1(C)). The gli1 plants accumulate near basal levels of SA/SAG, similar to the act1 and ssi2 sid2 plants, and expressed basal levels of PR-1 (FIGS. 8(B) and 1(C) and FIG. 4(C)).

These results further support the idea that inability to metabolize glycerol confers tolerance to glycerol and abolishes glycerol-induced defense responses.

Since glycerol treatment impacts the ACT1-catalyzed step (Kachroo et al., 2004), it is likely that the GK-generated G3P is channeled into the prokaryotic pathway of lipid biosynthesis. Applicants have shown that a reduction in G3P levels leads to the accumulation of 18:1 and reversion of ssi2 phenotypes in an age-dependent manner (Kachroo et al., 2004). In order to determine the relative contribution of GK towards the generation of G3P pools and its effect on ssi2 phenotypes, the gli1 mutation in the ssi2 background is mobilized and double mutant plants for various ssi2-like phenotypes are analyzed. During the initial stages of growth, the ssi2 gli1 double mutant plants are larger than ssi2 plants and develop fewer visible or microscopic cell death lesions on their leaves (FIGS. 8(D) and (E)). However, as in ssi2 glyl-3 plants, cell death lesions in these plants appear towards the later phase of growth (FIG. 8(E)). Unlike in ssi2 gly1-3 plants, absence of cell death in the ssi2 gli1 plants does not reduce or abolish constitutive expression of PR-1, which correlates with low levels of 18:1 (FIG. 8(F)), Table 3). These results suggest that although GLI1 also contributes to the G3P pool utilized in the prokaryotic pathway of lipid biosynthesis, it may not be the major source of the G3P pool. In addition, these results show that conversion of glycerol to G3P is required for the glycerol-mediated induction of defense, and that various genes contributing to G3P biosynthesis are likely to have a cumulative effect on ssi2-triggered phenotypes.

Plants Overexpressing G3PDH Show Enhanced Tolerance to a Hemibiotrophic Pathogen As a first step in determining the relationship between glycerol metabolism and disease resistance, it is assessed whether pathogen infection results in any change in the endogenous glycerol levels. Wild-type plants are inoculated with a virulent, hemibiotrophic pathogen, *Colletotrichum hiqginsianum* (O'Connell et al., 2004; Narusaka et al., 2004), and the glycerol levels are estimated 0, 1 and 3 days post-infection (dpi). The glycerol levels decline in a gradual manner after inoculation with *C. higginsianum* and are reduced by 50% at 3 dpi, in comparison to the water-treated controls (FIG. 1(B)). During necrotrophic development, hemibiotrophic pathogens, kill host tissues in advance of colonization and feed on the dead cells. Therefore, the decline in glycerol may be a result of the pathogen utilizing glycerol as a carbon source or the result of a pathogen-triggered signaling response in the host or both. Since the untreated gli1 plants accumulate ~3-fold higher levels of glycerol as compared to wt plants (FIG. 1(B)), gli1 plants are inoculated with *C. higginsianum* to determine if high levels of glycerol in these plants lead to increased pathogen growth and enhanced susceptibility. Interestingly, although gli1 plants show slightly bigger lesion size as compared to wt plants, they do not show any reduction in their glycerol content after pathogen inoculations (FIG. 1(B) and data not shown). This could be because gli1 plants are unable to metabolize glycerol to G3P, further suggesting that a glycerol-derived G3P may be involved in disease resistance. Next, the gly1 mutant are inoculated, which impacts the prokaryotic lipid pathway by lowering the G3P levels. Similar to gli1 the gly1 mutant also show enhanced susceptibility to *C. higginsianum* (data not shown). To ascertain if increased susceptibility in gly1 plants is associated with reduced G3P levels ill these plants, the GLY1-encoded G3PDH in Col-Q plants (35S-GLY1) is overexpressed. Two independent transgenic lines are analyzed and both lines show enhanced resistance to *C. higginsianum*; in comparison to Col-0, the 35S-GLY1 plants show smaller and fewer lesions on spot- and spray-inoculated leaves, respectively (FIGS. 1(D) and 1(E)). Microscopic examinations of these lesions show that pathogen inoculation on 35S-GLY1 cause hypersensitive-like cell death at the site of inoculation and is not associated with any mycelial proliferation (FIG. 1(F)). By comparison, Col-0 plants inoculated with *C. higginsianum* do not show any hypersensitive-like cell death and exhibit extensive proliferation of the pathogen (FIG. 1(F)). The spray-inoculated 35S-GLY1 plants show about a 3-fold lower PR-1 gene expression as compared to Col-0 plants (FIG. 1(G)). These results suggest an inverse relationship exists between PR-1 gene expression and resistance to hemibiotrophic pathogens.

To further confirm if increased levels of G3P produced as a result of glycerol utilization has any effect on 18:1 levels and the ACT1-catalyzed acylation reaction, the 18:1 content in water- and *C. higginsianum*-inoculated Col-O and act1 plants are analyzed. In comparison to the water sprayed plants, the pathogen inoculated Col-0 show -2-fold reduction in their 18:1 content at 12 h after inoculation (FIG. 1(C)). The 18:1 levels remain low till 72 h after inoculation and are restored at 96 h after inoculation. By comparison, the pathogen inoculated act1 plants do not show any alteration in their 18:1 content (data not shown). This suggests that *C. higginsianum* inoculation results in an increase in G3P levels, which has a quenching effect on 18:1. Taken together, these results suggested that host G3P levels play a key role in defense signaling.

Discussion of Exemplary Results

Exogenous glycerol application to wild type (wt) plants causes accumulation of SA and induction of PR genes, which suggests that the SA pathway is upregulated in these plants. These finding are further supported by the observations that both the sid2 mutation and the expression of the nahG transgene are able to abolish glycerol-mediated increases in SA and PR expression (FIGS. 3(B) and (C)).

Figure 3E:
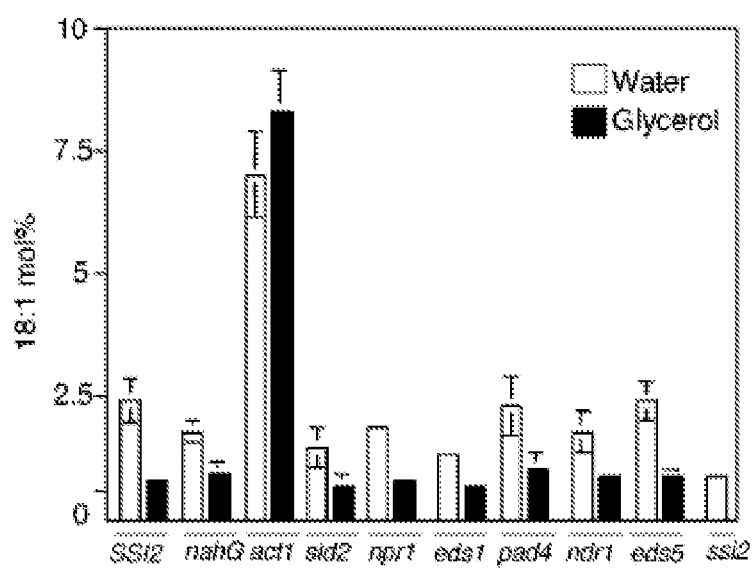

FIGS. 3(A)-3(C) illustrate glycerol-mediated effects on mutants impaired in SA or R-gene signaling, where FIG. 3(A) comprises a series of microscopies of trypan blue-stained leaves from indicated genotypes treated with water or 50 mM glycerol. FIG. 3(B) is a plot illustrating endogenous SA and SAG levels in the leaves of indicated 4-week-old soil-grown plants treated with water or glycerol. FIG. 3(C) shows expression of the PR-1 and PR-2 genes in indicated genotypes, in which RNA gel blot analysis was performed on 7 pg of total RNA extracted from 4-week-old soil-grown plants treated with water or glycerol. Ethidium bromide staining of rRNA used as a loading control. FIG. 3(D) is a graph showing growth of *P. parasitica* biotype Emco5 on various plant genotypes listed at the left. The Landsberg (Ler) ecotype used as the resistant control. The plants were treated with water (W) or glycerol (G) for 72 h prior to pathogen inoculations and about 60-75 cotyledons were scored for infection. The shade of each box indicates the severity of infection, based on the number of sporangiophores per cotyledon (see key at the right). FIG. 3(E) is a plot showing glycerol-induced changes in the 18:1 levels in leaf tissue of 4-week-old plants. Plants were treated with glycerol or water, and samples taken 72 h post-treatment were analyzed for FAs using gas chromatography (GC).

However, both sid2 and nahG plants show glycerol-induced leaf cell death, thus disassociating SA accumulation and cell death. The defense phenotypes induced upon glycerol application to mutants impaired in R-gene and SA signaling are similar to the phenotypes seen in ssi2 double mutants containing the respective alteration in R-gene or SA pathway. For example, ssi2 sid2 and ssi2 nahG plants show cell death and show basal level expression of PR-1 gene (FIGS. 4(B) and 4(C)). In addition, similar to glycerol-treated npr1 and eds5 plants, the ssi2 npr1 and ssi2 eds5 plants show an increase in PR-2 and a decrease in PR-1 expression (FIG. 3(C) and FIG. 4(D)). Similarly, all the glycerol-treated genotypes and ssi2 eds1, ssi2 pad4, ssi2 eds5, ssi2 ndr1, ssi2 sid2 and ssi2 nahG plants show low levels of 18:1, which are comparable to those seen in ssi2 plants (FIG. 3(E) and Table 1). These observations suggest that glycerol-triggered signaling is similar to that induced by the ssi2 mutation.

A comprehensive analysis of ssi2 phenotypes in double or triple mutant backgrounds defective in SA signaling, R-gene signaling or FA desaturation steps, show that several of these mutations have an effect on the ssi2 morphological phenotype. The ssi2 eds1, ssi2 eds5, ssi2 pad4, ssi2 sid2, and ssi2 nahG plants are larger, most likely due to the reduction of SA/SAG levels (FIGS. 4(A) and 4(C)).

FIG. 4 illustrates morphological, molecular and biochemical phenotypes of wild type (wt), ssi2, ssi2 nahG, ssi2 sid2, ssi2 pad4, ssi2 eds1, ssi2 eds5 and ssi2 ndr1 plants. FIG. 4(A) comprises a series of photographs showing a comparison of the morphological phenotypes displayed by the wt, ssi2 and various double mutant plants in the ssi2 background. FIG. 4(B) comprises a series of microscopies of trypan blue-stained leaves from wt, ssi2 and various double mutant plants in the ssi2 background. FIG. 4(C) is a plot showing endogenous SA and SAG levels in the leaves of indicated 4-week-old soil-grown plants treated with water or glycerol. FIG. 4(D) illustrates expression of the PR-1 and PR-2 genes in indicated genotypes. RNA gel blot analysis performed on 7 μg of total RNA extracted from 4-week-old soil-grown plants. Ethidium bromide staining of rRNA was used as a loading control. FIG. 4(E) is a plot showing growth of P. parasitica biotype Emco5 on various plant genotypes listed at the left. The Landsberg (Ler) and Nossen (No) ecotypes were used as the resistant and susceptible controls, respectively. The numbers against each box indicate cotyledons scored. The shade of each box indicates the severity of infection, based on the number of sporangiophores per cotyledon, as shown in the key in FIG. 4(E).

However, none of these restore the altered SA- and JA-mediated signaling in the ssi2 plants (FIG. 4). Besides the SA-signaling mutants, mutations in fad7 and fad7 fad8 are also able to reduce SA/SAG levels in the ssi2 plants (FIG. 5(H)). Although the fad7 and fad7 fad8 mutations down regulate ssi2-triggered PR-2 gene expression, these mutations are unable to restore SA- or JA-mediated defenses in ssi2 plants (FIGS. 5(F), 5(G) and 5(I)). One possible explanation for these observations would be that fad7 and fad7 fad8 mutations allow increased accumulation of 18:1 in ssi2 plant, which partially restores the ssi2-triggered phenotypes. Since fad7 and fad8 mutations block the step leading to the synthesis of 18:3 in plastidal lipids, these mutations might cause a "back-up" effect, resulting in the accumulation of an 18:1 precursor. This idea is supported by the observation that 18:1 levels in fad7 and fad7 fad8 mutants are higher than in the wt plants. Similarly, the 18:1 levels in ssi2 fad7 and ssi2 fad7 fad8 plants are consistently higher compared to those of the ssi2 plants as shown in Table 2. The fad7 and fad7 fad8 plants also showed a slower and less drastic decline in their 18:1 levels upon exogenous application of glycerol (FIG. 5(D) and data not shown). However, this does not explain why fad6 plants are not as tolerant to glycerol as the fad7 or fad7 fad8 plants. Interestingly, the partial restoration of phenotypes displayed by ssi2 fad7 and ssi2 fad7 fad8 plants are similar to those seen in ssi2 fad6 (Kachroo et al., 2003b). The fad6 mutants have increased accumulation of 18:1 in membranous lipids, thus it is likely that this mutation causes a similar "back-up" effect resulting in accumulation of free 18:1 in the plastids.

Figure 5A:
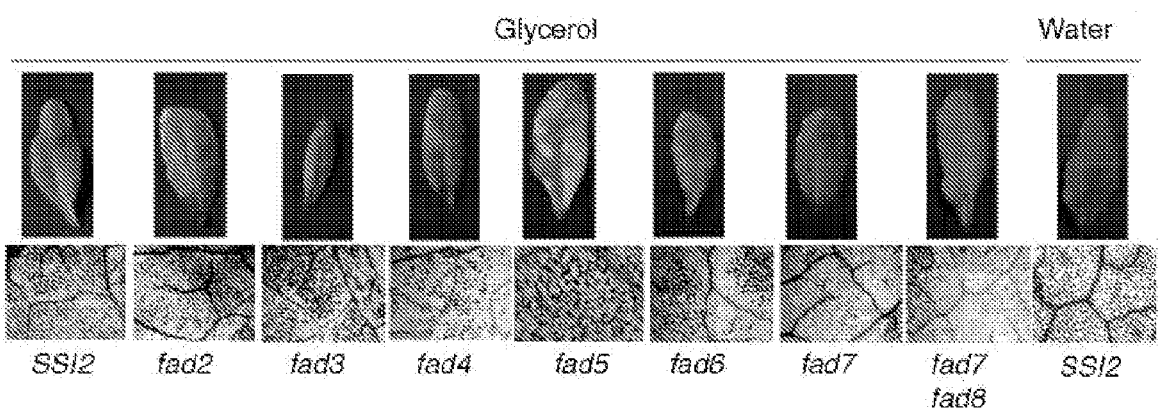
FIGS. 5(A)-5(I) illustrate glycerol-mediated effects on mutants impaired in various fatty add desaturation (fad) steps and double mutant analysis of ssi2 in different fad backgrounds where FIG. 5(A) comprises a series of photographs showing the morphological and cell death phenotypes displayed by the wt, fad2, fad3, fad4, fad5, fad6, fad7, and fad7 fadB plants.
Figure 5B:
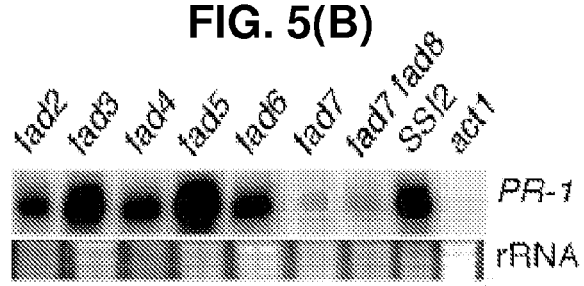
Figure 5C:
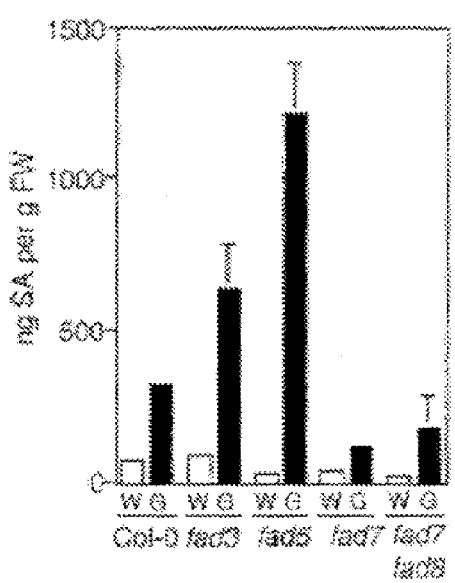

In comparison to fad7, the fad5 and fad3 plants accumulate higher levels of SA than wt upon exogenous application of glycerol (FIG. 5(C)).

Figure 5D:
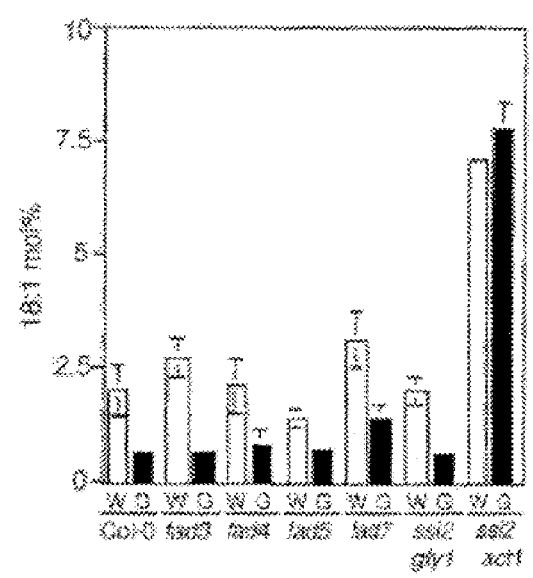
Figure 5E:
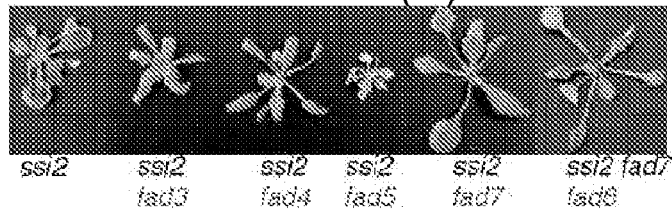
Figure 5F:
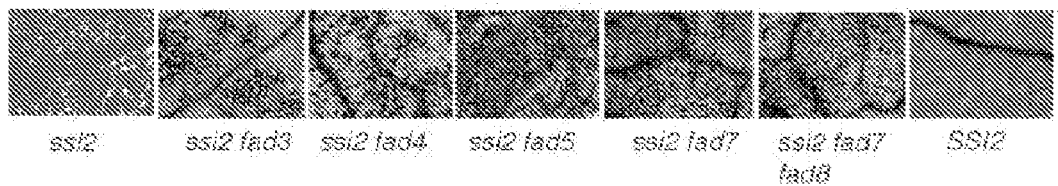
Figure 5G:
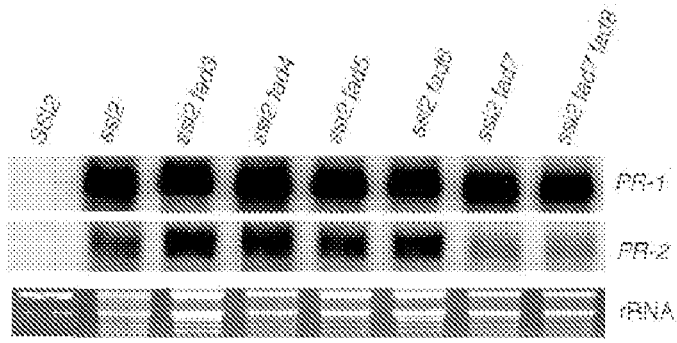
Figure 5H:
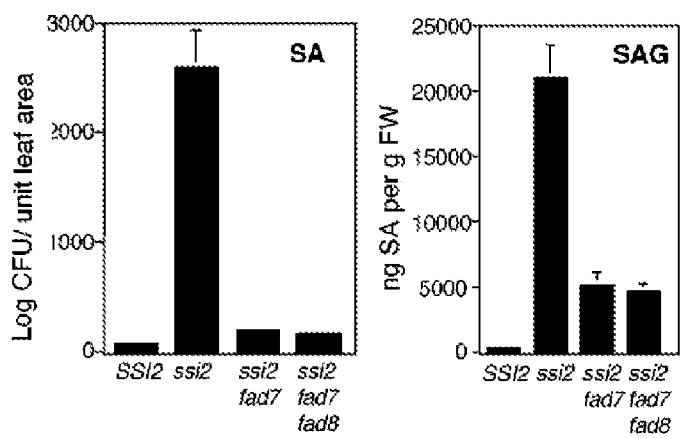
Figure 5I:
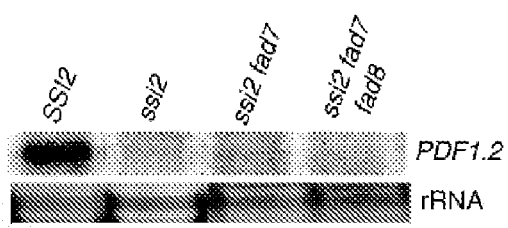

FIGS. 5(A)-5(I) illustrate glycerol-mediated effects on mutants impaired in various fatty add desaturation (fad) steps and double mutant analysis of ssi2 in different fad backgrounds. FIG. 5(A) illustrates a comparison of the morphological and cell death phenotypes displayed by the wt, fad2, fad3, fad4, fad5, fad6, fad7, and fad7 fadB plants. FIG. 5(B) shows expression of the PR-1 gene in glycerol-treated fads, wt and act1 plants. RNA gel blot analysis was performed on 7 μg of total RNA extracted from 4-week-old soil-grown plants. Ethidium bromide staining of rRNA was used as a loading control. FIG. 5(C) is a plot showing endogenous SA levels in the leaves of 4-week-old soil-grown wt (Col-O), fad3, fad5, fad7 and fad7 fadB plants treated with water (W) or glycerol (G). The values presented are averages of three replicates. FIG. 5(D) is a plot showing glycerol-induced changes in the 18:1 levels in leaf tissue of four-week-old plants. The ssi2 gly1and ssi2 act1 plants were used as controls. Plants were treated with glycerol (G) or water (W), and samples taken 72 h post-treatment were analyzed for FAs using gas chromatography (GC). FIG. 5(E) illustrates a comparison of the morphological phenotypes displayed by the ssi2 and various ssi2 fad double and triple mutant plants. FIG. 5(F) comprises a series of microscopies of trypan blue-stained leaves from ssi2 and various ssi2 fad double- and triple-mutant plants. FIG. 5(G) illustrates expression of the PR-1 and PR-2 genes in wt, ssi2, and various ssi2 fad double and triple mutant plants. RNA gel blot analysis was performed on 7 μg of total RNA extracted from 4-week-old soil-grown plants. Ethidium bromide staining of rRNA was used as a loading control. FIG. 5(H) is a plot showing endogenous SA and SAG levels in the leaves of 4-week-old soil grown 88/2, ssi2, ssi2 fad7 and ssi2 fad7 fad8 plants. FIG. 5(I) illustrates expression of the PDF1.2 gene in SSI2, ssi2, ssi2 fad7 and ssi2 fad7 fad8 plants in response to 50 μM JA. Samples were harvested 48 h post treatment and analyzed by RNA gel blot analysis performed on 7 μg of total RNA. Ethidium bromide staining of rRNA was used as a loading control.

However, unlike fad5, the fad5 plants does not show hypersensitivity towards glycerol (FIG. 5(A)). Introduction of the fad5 mutation in the ssi2 plants enhances their morphological severity and cell death phenotypes, but does not affect the levels of PR gene expression in these plants (FIGS. 5(E), 5(F) and 5(G)). One possible explanation is that FAD5 or FAD5-derived component(s) act to balance the negative effects caused by the ssi2 mutation, and the absence of these accentuates the effects of the ssi2 mutation. These results further demonstrate common features between glycerol- and ssi2-mediated effects. Epistatic analysis between ssi2 and various fad genes show that these mutations are unable to restore altered defense signaling in the ssi2 plants. Since ssi2 or glycerol-treated wt or act1 plants do not show any change in PA levels, respectively, Applicants suggest that 18:1-mediated signaling is not associated with alterations in PA levels (FIG. 6(A)). This is further supported by the double mutant analysis of ssi2 dgd1 plants, which show all the ssi2-related phenotypes (FIG. 6(B)).

Figure 6A:
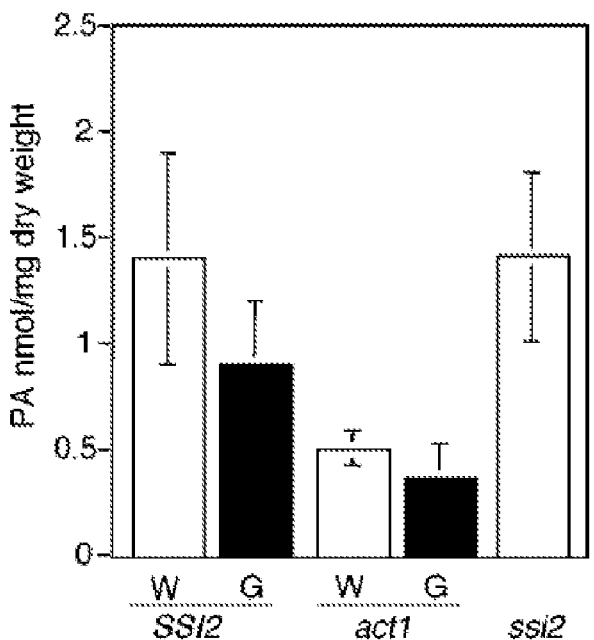
FIGS. 6(A)-6(D) depicting PA levels and morphological and molecular analyses of ssi2 dgd1 plants where FIG. 6(A) corresponds to PA levels in ssi2 and wt (Col-0) and act1 plants treated with water or glycerol.
Figure 6B:
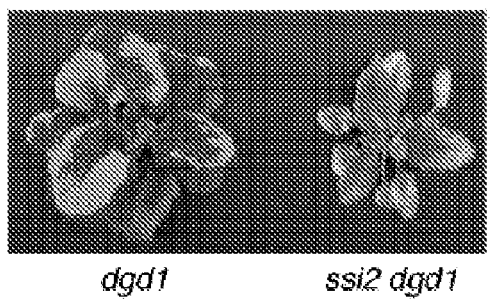
Figure 6C:
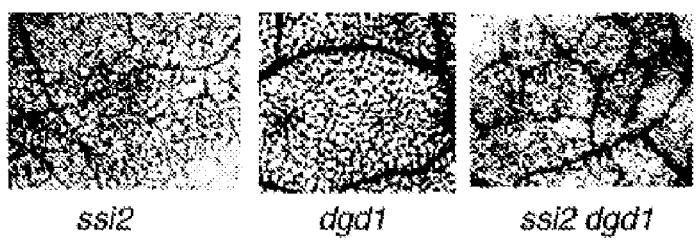
Figure 6D:
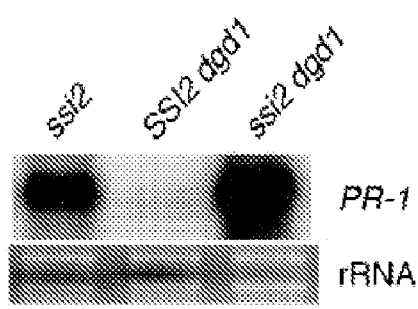

FIGS. 6(A)-6(D) illustrate PA levels and morphological and molecular analyses of ssi2 dgd1 plants. FIG. 6(A) is a plot showing PA levels in ssi2 and wt (Col-0) and act1 plants treated with water (W) or glycerol (G). FIG. 6(B) illustrates a comparison of the morphological phenotypes displayed by the 4-week-old soil-grown dgd1 and ssi2 dgd1 plants. FIG. 6(C) comprises a series of microscopies of trypan blue-stained leaves from ssi2, dgd1, and ssi2 dgd1 plants. FIG. 6(D) illustrates expression of the PR-1 gene in ssi2, dgd1 and ssi2 dgd1 plants. RNA gel blot analysis was performed on 7 μg of total RNA extracted from 4-week-old soil-grown plants. Ethidium bromide staining of rRNA was used as a loading control.

Act1 plants are unable to induce a defense response upon exogenous treatment with glycerol (Kachroo et al., 2004). This was attributed to their inability to acylate 18:1 on a G3P backbone, which would allow retention of the 18:1 pool in plastids. The exemplary studies described herein show that the gli1 mutant plants behave similarly to act1 plants, neither reducing their 18:1 levels nor inducing SA or PR gene expression upon glycerol application (FIGS. 8(A)-(C)).

Figure 8A:
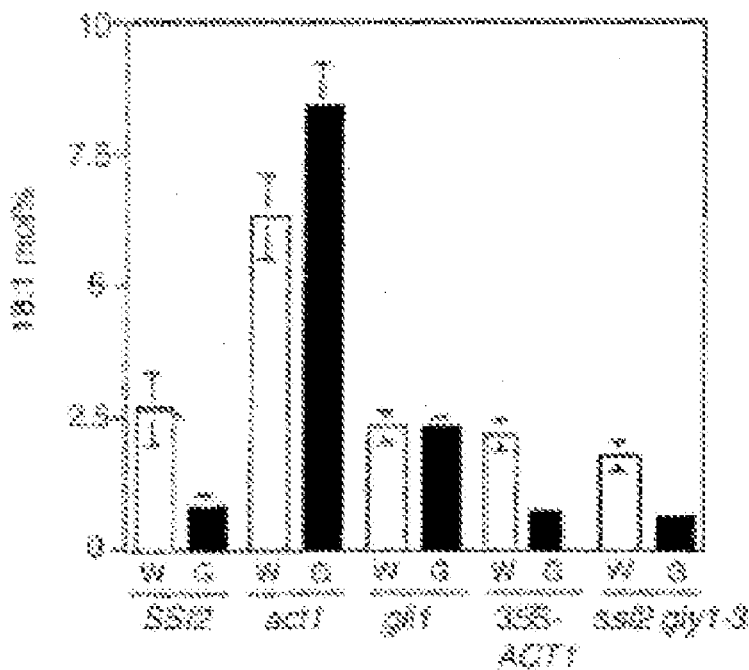
FIGS. 8(A)-8(E) illustrate a comparison of glycerol-responsiveness in wild type, act1, gli1, ssi2 gly1-3 and 35S-ACT1 plants and double mutant analysis of ssi2 gli1 plants where
Figure 8B:
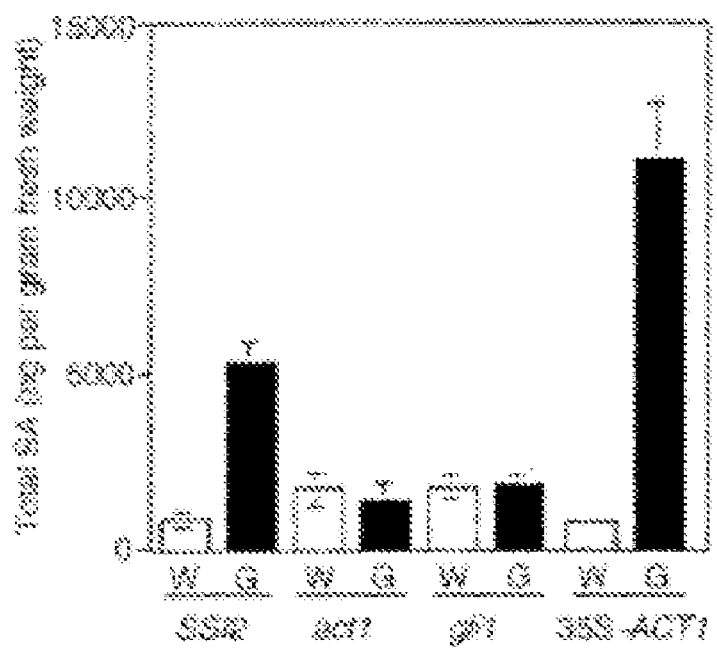
Figure 8C:
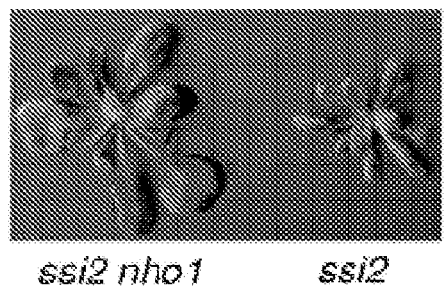
Figure 8:
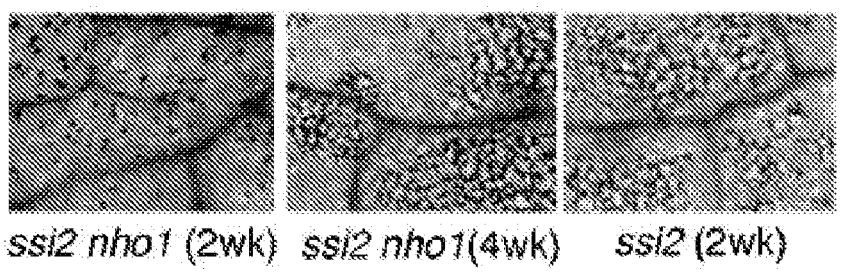
Figure 8E:
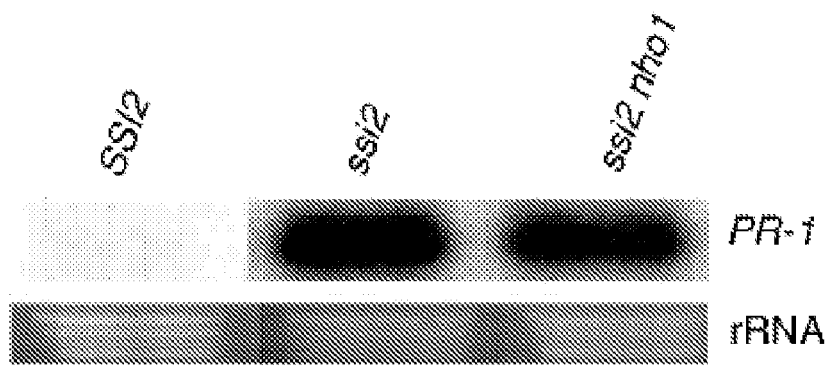

FIGS. 8(A)-8(F) show a comparison of glycerol-responsiveness in wild type, act1, gli1, ssi2 gly1-3 and 35S-ACT1 plants and double mutant analysis of ssi2 gli1 plants. FIG. 8(A) is a plot showing glycerol-induced changes in the 18:1 levels in leaf tissue of 4-week-old plants. Plants were treated with glycerol (G) or water (W), and samples taken 72 h post-treatment were analyzed for 18:1 content using GC. The values shown are an average of six independent replicates. FIG. 8(B) is a plot showing endogenous SA and SAG levels in the leaves of 4-week-old soil-grown plants. The values presented are averages of three replicates. FIG. 8(C) illustrates expression of the PR-1 gene in glycerol-treated plants. RNA gel blot analysis was performed on 7119 of total RNA extracted 72 h after glycerol treatment. Ethidium bromide staining of rRNA was used as a loading control. FIG. 8(D) shows a comparison of the morphological phenotypes displayed by the 16-day-old soil-grown ssi2 and ssi2 gli1 plants. FIG. 8(E) comprises a series of microscopies of trypan blue-stained leaves from ssi2 and various ssi2 gli 1 plants. FIG. 8(F) illustrates expression of the PR-1 gene in ssi2 and ssi2 gli1 plants. RNA gel blot analysis was performed on 7 μg of total RNA extracted from 16-day-old soil-grown plants. Ethidium bromide staining of rRNA was used as a loading control.

A link between 18:1 levels and the SA pathway is further established by analyzing the effects of glycerol on plants overexpressing ACT1. The 35S-ACT1 plants induce higher levels of SA and PR gene expression upon glycerol treatment. Since GLI1 encodes a glycerol kinase, the gil1-defective plants are likely to synthesize reduced amounts of G3P. However, unlike the gly1 (defective in G3PDH) plants, a mutation in gli1 does not affect the prokaryotic pathway of lipid biosynthesis. This suggests that G3P required for the prokaryotic pathway is largely derived from GLI1-independent pathway(s). The Arabidopsis genome contains several isoforms of G3PDH and these are probably involved in maintaining the cellular pools of G3P. The presence of these isozymes in various cellular compartments is likely to involve an exchange of G3P between the cytoplasm and plastids. This is further supported by the observation that ssi2 gli1 plants show partial restoration of morphology and cell death phenotypes (See FIG. 8(D)). A reduction in cytosolic G3P levels caused by the gli1 mutation may not be sufficient to affect the plastidal G3P pool, but may be sufficient to affect the ssi2 phenotypes.

The observation that C. higginsianum inoculation caused a decline in glycerol levels in wt, but not in gli1, plants suggest that the glycerol is mostly being utilized by the plant and not by the pathogen (FIG. 1(B)).

The observation that C. higginsianum inoculation caused a decline in glycerol levels in wt, but not in gti1, plants suggets that the glycerol is mostly being utilized by the plant and not by the pathogen (FIG. 1(B)).

Figure 1C:
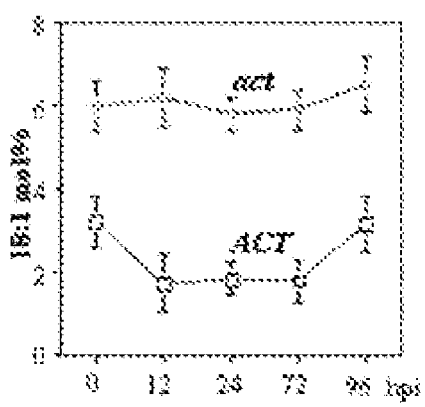
Figure 1D:
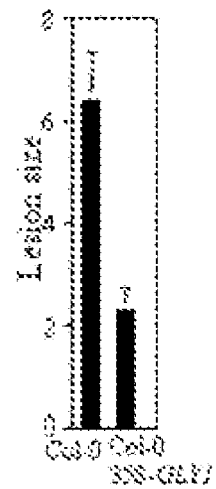
Figure 1E:
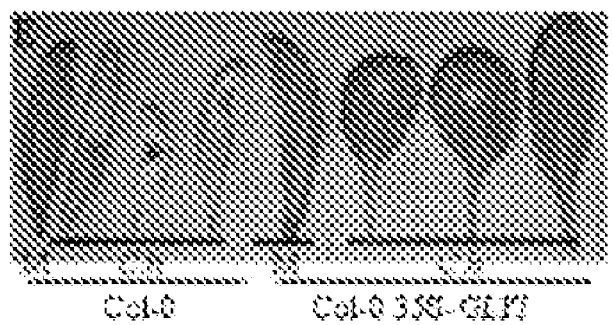
Figure 1F:
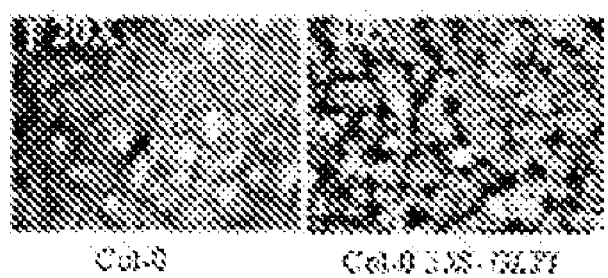
Figure 1G:
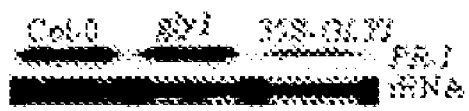

FIGS. 1(A)-1(F) illustrate glycerol levels and host response after pathogen inoculations. FIG. 1(B) is a plot showing glycerol levels in wt (Col-O) and gli1 plants 72 h after inoculations with water or C. higginsianum spores. FIG. 1(D) is a plot showing lesion size in wt (Col-0) and 35S-GLY1 plants. The lesion size was determined 5 days post-inoculation (dpi) with C. higginsianum. FIG. 1(E) illustrates morphological phenotypes displayed by the mock (M) or C. higginsianum (C. h)-inoculated leaves from Col-O and 35S-GLY1 plants at 5 dpi. FIG. 1(F) comprises a series of microscopies of trypan blue-stained leaves from Col-O and 35S-GLY1 plants inoculated with water (mock) or C. higginsianum. The leaves show the inoculated spot at two different magnifications. The profuse branching of mycelia in pathogen inoculated Col-O leaf is indicated by a black arrow and the non-germinating spores on 35S-GLY1 leaf is indicated by a white arrowhead. FIG. 1(G) illustrates expression of the PR-1 gene in C. higginsianum inoculated plants. RNA gel blot analysis was performed on 7 μg of total RNA extracted 96 h after spray inoculation. Ethidium bromide staining of rRNA was used as a loading control. FIG. 1(C) is a plot showing pathogen-induced changes in the 18:1 levels in leaf tissue of 4-week-old plants. Plants were treated with C. higginsianum, and samples taken 0, 12, 24, 72 and 94 h after inoculation were analyzed for FAs using GC.

However, it is possible that, in addition to other nutrients, the pathogen also utilizes some of the glycerol in host cells. This is supported by Wei et al.'s (2004) work where they showed that growth defects in a G3PDH mutant of C. gloeosporioides were entirely ameliorated by providing glycerol in the artificial medium or by allowing it to grow in plants. If C. higginsianum is making substantial use of glycerol for its growth or sporulation on Arabidopsis, a significantly greater development of the pathogen in gli1 plants would have been expected to be seen, since these plants accumulate about a 3-fold higher levels of glycerol. Because C. higginsianum is only slightly more virulent on gli1 plants, pathogen utilization is probably not the major reason for reduction of glycerol levels in infected plants.

One plausible explanation accounting for utilization of glycerol in wt, but not in gli1 plants would be that the pathogen triggers the conversion of glycerol into G3P by the plant and that a defective glycerol kinase in gli1 is unable to utilize glycerol and generate G3P. Thus, it is conceivable that accumulation of G3P or a G3P-derived metabolite proves advantageous to the plant during pathogen infection. This possibility is supported by several observations. First, the act1 plants, which are likely to accumulate higher levels of G3P, show slightly enhanced resistance towards C. higginsianum infection. Secondly, the gli1 and gly1 plants are slightly more susceptible to C. higginsianum. Thirdly, overexpression of GLY1 results in pronounced resistance to C. higginsianum.

The gly1 mutation results in lower G3P levels, causing accumulation of 18:1. This increase in 18:1 levels restores the SA- and JA-mediated signaling in ssi2 gly1 plants (Kachroo et al., 2004). Thus, an increase in the G3P levels generated by overexpression of GLY1 should cause depletion of 18:1 and converted wt plants into ssi2 mimics. However, overexpression of GLY1 does not cause any altered morphological, cell death or PR overexpression phenotypes. Furthermore, the 18:1 levels in 35S-GLY1 plants are similar to the wt plant. These results indicate that overexpression of GLY1 does not effect ACT1-catalyzed acylation step. It is possible that GLY1overexpression results in only a small increase in the G3P levels due to substrate limitations. This is supported by the observation that ACT1-catalyzed step is limiting and 35S-ACT1 plants do not show a severe phenotype unless sprayed with glycerol (FIG. 6A-C, Kachroo et al., 2004). Another possibility is that G3P generated by GLY1 overexpression is channeled elsewhere and is not available for the ACT1-catalyzed reaction. There are at least two possible scenarios, which can account for enhanced resistance of 35S-GLY1 lines to C. higginsianum. In the first scenario, overexpression of GLY1 generates higher levels of G3P in pathogen-inoculated plants, which leads to resistance. A second possibility is that a G3P-derived metabolite is required for resistance and is generated as a result of the oxidative activity of GLY1-encoded G3PDH. Since the G3PDH oxidation or reduction activity depends on relative pools of G3P and DHAP, respectively, a higher level of G3P is likely to favor the oxidative reaction FIG. 9. The DHAP generated in the plant system can be converted to dihydroxyacetone or glyceraldehyde-3-phosphate (GAPdh), both of which are reversible reactions. Thus, a shift in balance between G3P and DHAP is likely to affect several different metabolic reactions besides altering the levels of 18:1. A reduction in 18:1 levels upon glycerol application of 35S-GLY1 plants suggests that the ACT1-catalyzed step functions normally in these plants (data not shown). Thus, it is possible that G3P generated as a result of glycerol utilization in pathogen-inoculated plants is mostly directed towards formation of G3P-derived metabolites. This is supported by the observation that C. hiagginsianum inoculated 35S-GLY1 plants do not show a reduction in 18:1 levels. A link between G3P-mediated signaling and defense is further suggested by the observation that nitric oxide-mediated nitrosylation can cause reversible inhibition of GAPdh (Lindermayr et al, 2005).

The exemplary studies described herein demonstrate that 18:1 and G3P are metabolites whose levels play a role in the regulation of defense signaling pathways. Interestingly, G3P levels can regulate 18:1 content without causing an altered flux in plastidal or extraplastidal lipids. An alteration in 18:1 caused by an increase in G3P levels after *C. higginsianum* infection is restored at 96 h post-inoculation, suggesting that the changes in G3P and 18:1 are transitory in nature, further supporting their role as signaling molecules.

It is intended that the Specification and Examples be considered as exemplary only, and not intended to limit the scope and spirit of the invention. Unless otherwise indicated, all numbers expressing quantities of ingredients, properties such as reaction conditions, and so forth used in the Specification are to be understood as being modified in all instances by the term "about." Accordingly, unless indicated to the contrary, the numerical parameters set forth in the Specification are approximations that may vary depending upon the desired properties sought to be determined by the present invention.

Notwithstanding that the numerical ranges and parameters setting forth the broad scope of the invention are approximations, the numerical values set forth in the experimental or examples section are reported as precisely as possible. Any numerical value, however, inherently contain certain errors necessarily resulting from the standard deviation found in their respective testing measurements.

Throughout this application, various publications are referenced. All such references are incorporated herein by reference.

REFERENCES

Bowling, S. A., Clarke, J. D., Liu, Y., Klessig D. F. and Dong X. (1997) The cpr5 mutant of *Arabidopsis* expresses both NPR1-dependent and NPR1-Independent resistance. Plant Cell 9, 1573-1584.

Cao, H., Glazebrook, J., Clarke, J. D., Volko, S. and Dong, X. (1997) The *Arabidopsis* NPR1 gene that controls systemic acquired resistance encodes a novel protein containing ankyrin repeats. Cell 88, 57-63.

Chandra-Shekara, A. C, Navarre D., Kachroo, A., Kang, H-G., Klessig D. F., Kachroo, P. (2004) Signaling requirements role of salicylic acid in HRT- and rrt-mediated resistance to turnip crinkle virus in *Arabidopsis*. Plant J. 40, 647-659.

Dahmer, M. L., Fleming, P. D., Collins, G. B. and Hildebrand, D. F. (1989) A Rapid screening for determining the lipid composition of soybean seeds. J. Am. Oil Chem. 66, 534-538.

De Jong, C. F., Laxalt, A. M., Bargmann, B. O. R., de wit, P. J. G. M., Joosten, M, H. A. J. and Munnik, T. (2004) Phosphatidic acid accumulation is an early response in the Cf-4/Avr4 interaction. Plant J. 39, 1-12.

Delaney, T .P., Uknes, S., Vernooij, B., Friedrich, L., Weymann, K., Negrotto, D., Gaffney, T., Gut-Rella, M., Kessmann, H., Ward, E., et al. (1994) A central role of salicylic acid in plant disease resistance. Science 266, 1247-1250.

Durrant, W. E. and Dong, X. (2004) Systemic acquired resistance. Annu. Rev. Phytopathol. 42, 185-209.

Eastmond, P. J. (2004) Glycerol-insensitive *Arabidopsis* mutants: gli1 seedlings lack glycerol kinase, accumulate glycerol and are more resistant to abiotic stress. Plant J. 37, 617-625.

Falk, A., Feys, B. J., Frost, L. N., Jones J. D. G., Daniels M. J. and Parker, J. E. (1999) EDS1, an essential component of R gene mediated disease resistance in *Arabidopsis* has homology to eukaryotic lipases. Proc. Natl. Acad. Sci. USA 96, 3292-3297.

Gaffney, T., Friedrich, L., Vernooij, B., Negrotto, D., Nye, G., Uknes, S., Ward, E., Kessmann, H. and Ryals, J.A. (1993) Requirement of salicylic acid for the induction of systemic acquired resistance. Science 261, 754-756.

Gerber, D. W., Byerrum, R. U., Gee, R. W. and Tolbert, N. E. (1988) Glycerol concentration in crop plants. Plant Sci. 56, 31-38.

He, Y., Fukushige, H., Hildebrand, D. F. and Gan, S. (2002) .Evidence supporting a role of jasmonic acid in *Arabidopsis* leaf senescence. Plant Physiol. 128, 876-884.

Jirage, D., Tootle, T. L., Reuber, T. L., Frost, L. N., Feys, B. J., Parker, J. E., Ausubel, F. M. and Glazebrook, J. (1999) *Arabidopsis thaliana* PAD4 encodes a lipase-like gene that is important for salicylic acid signaling. Proc. Natl. Acad. Sci. USA 96, 13583-13588.

Kachroo, P., Shanklin, J., Shah, J., Whittle, E. J. and Klessig, D. F. (2001) A fatty acid desaturase modulates the activation of defense signaling pathways in plants. Proc. Natl. Acad. Sci. USA 98, 9448-9453.

Kachroo, P., Kachroo, A., Lapchyk, L., Hildebrand, D. and Klessig, D. (2003a) Restoration of defective cross talk in ssi2 mutants: role of salicylic acid, jasmonic acid and fatty acids in SSI2-mediated signaling. Mol. Plant Microbe Interact. 16, 1022-1029.

Kachroo, A., Lapchyk, L., Fukushigae, H., Hildebrand, D., Klessig, D. F. and Kachroo, P. (2003b) Plastidial fatty acid signaling modulates salicylic acid- and jasmonic acid-mediated defense pathways in the *Arabidopsis* ssi2 mutant. Plant Cell 15, 2952-2965.

Kachroo, A., Srivathsa C. V., Lapchyk, L., Falcone, D., Hildebrand, D. and Kachroo, P. (2004) Oleic acid levels regulated by glycerolipid metabolism modulate defense gene expression in *Arabidopsis*. Proc. Natl. Acad. Sci. USA. 101, 5152-5157.

Kachroo, A., Venugopal, S. C., Lapchyk, L., Falcone, D., Hildebrand, D. and Kachroo, P. (2004) Oleic acid levels regulated by glycerolipid metabolism modulate defense gene expression in *Arabidopsis*. Proc. Natl. Acad. Sci. USA 101, 5152-5157.

Kang, L., Li, J., Zhao, T., Xiao, F., Tang, X., Thilmony, R., He, S. .and Zhou J. M. (2003) Interplay of the *Arabidopsis* nonhost resistance gene NH01 with bacterial virulence. Proc. Natl. Acad. Sci. USA 100, 3519-3524.

Klaus, D., Hartel, H., Fitzpatrick, L. M., Froehlich, ~.E., Hubert, J., Benning, C. and Dormann, P.(2002) Digalactosyldiacylglycerol synthesis in chloroplasts of the *Arabidopsis* dgd1 mutant. Plant Physiol. 128, 885-895.

Kunst, L., Browse, J. and Somerville, C. (1988) Altered regulation of lipid biosynthesis in a mutant of *Arabidopsis* deficient in chloroplast glycerol-3-phosphate acyltransferase activity. Proc. Natl. Acad. Sci. USA 85, 4143-4147.

Li, C., Liu, G., Xu, C., Lee, G. I., Bauer, P., Ling, H. Q., Ganal, M. W., Howe, G. A. (2003) The tomato suppressor of prosystemin-mediated responses2 gene encodes a fatty acid desaturase required for the biosynthesis of jasmonic acid and the production of a systemic wound signal for defense gene expression. Plant Cell 15, 1646-1661.

Lindermayr, C., Saalbach,.G. and Durner, J. (2005) Proteomic identification of S-nitrosylatedproteins in *Arabidopsis*. Plant Physiol. 137, 921-930.

McDowell, J. M., Dhandaydham, M., Long, T. A., Aarts, M. G., Goff, S., Holub, E. B. and Dangl J. L. (1998) Intragenic recombination and diversifying selection contribute to the evolution of downy mildew resistance at the RPPBlocus of *Arabidopsis*. Plant Cell, 10, 1861-1874.

Miguel, M., Cassagne, C. and Browse, J. (1998) A new class of *Arabidopsis* mutants with reduced hexadecatrienoic acid fatty acid levels. Plant Physiol. 117, 923-930.

Miguel, M. (2003) What is new about glycerol metabolism in plants? In: Advanced Research on Plant Lipids, N. Murata et al. (eds), Kluwer Academic Publishers, Dordrecht, Netherlands. pp 45-47.

Nandi, A., Welti, R. and Shah, J. (2004) The *Arabidopsis thaliana* dihydroxyacetone phosphate reductase gene SUPPRESSSOR OF FATTY ACID DESATURASE DEFICIENCY1 is required for glycerolipid metabolism and for the activation of systemic acquired resistance. Plant Cell 16, 465-477.

Narusaka, Y., Narusaka, M., Park, P., Kubo, Y., Hirayama, T., Seki, M., Shiraishi, T., Ishida, J., Nakashima, M., Enju, A., Sakurai, T., Satou, M., Kobayashi, M. and Shinozaki K. (2004) RCH1, a locus in *Arabidopsis* that confers resistance to the hemibiotrophic fungal pathogen *Colletotrichum higginsianum*. Mol. Plant-Microbe Interact. 17, 749-762.

Nawrath, C., Heck, S., Parinthawong, N. and Metraux, J. P. (2002) EDS5, an essential component of salicylic acid-dependent signaling for disease resistance in *Arabidopsis*, is a member of the MATE transporter family. Plant Cell 14, 275-286.

O'Connell, R., Herbert, C., Sreenivasaprasad, S., Khatib, M., Esquerre-Tugaye, M. T. and Dumas, B. (2004) A novel *Arabidopsis*-*Colletotrichum* pathosystem for the molecular dissection of plant-fungal interactions. Mol. Plant-Microbe Interact. 17, 272-282.

Ohlrogge, J., and Browse, J. (1995) Lipid biosynthesis. Plant Cell 7, 957-970.

Ryals, J., Weymann, K., Lawton, K., Friedrich, L., Ellis, D., Steiner, H. Y., Johnson, J., Delaney, T. P., Jesse, T., Vos, P., et al. (1997) The *Arabidopsis* NIM1 protein shows homology to the mammalian transcription factor inhibitor I kappa B. Plant Cell 9, 425-439.

Shah, J., Kachroo, P., Nandi, A. and Klessig D. F. (2001) A recessive mutation in the *Arabidopsis* SSI2 gene confers SA- and NPR1-independent expression of PR genes and resistance against bacterial and oomycete pathogens. Plant J. 25, 563-574.

Shah, J., Tsui, F. and Klessig, D. F. (1997) Characterization of a salicylic acid- insensitive mutant (sai1) of *Arabidopsis thaliana*, identified in a selective screen utilizing the SA-inducible expression of the tms2 gene. Mol. Plant Microbe Ineract. 1, 69-78.

Shen, W., Wei, Y., Dauk, M., Zheng, Z. and Zou, J. (2003) Identification of a mitochondrial glycerol-3-phosphate dehydrogenase from *Arabidopsis thaliana*: evidence for a mitochondrial glycerol-3-phosphate shuttle in plants. FEBS lett. 536, 92-96.

Vijayan, P., Shockey, J., Levesque, C. A., Cook, R. J. and Browse, J. (1998) A role for jasmonate in pathogen defence of *Arabidopsis*. Proc. Natl. Acad. Sci. USA 95, 7209-7214.

Weber, H. (2002) Fatty acid derived signals in plants. Trends Plant Sci. 7, 217-224.

Wei, Y., Periappuram, C., Datla, R., Selvaraj, G. and Zou, J. (2001) Molecular and biochemical characterization of a plastidic glycerol-3-phosphate dehydrogenase from *Arabidopsis*. Plant Physiol. Biochem. 39, 841-848.

Wei, Y., Shen, W., Dauk, M., Wang, F., Selvaraj, G. and Zou J. (2004) Targeted gene disruption of glycerol-3-phosphate dehydrogenase in *Colletotrichum gloeosporioides* reveals evidence that glycerol is a significant transferred nutrient from host plant to fungal pathogen. J. Biol. Chem. 279, 429-435

Welti, R., Li, W., Li, M., Sang, Y., Biesiada, H., Zhou, H. E., Rajashekar, C. B., Williams, T. D. and WangX. (2002) Profiling membrane lipids in plant stress responses. Role of phospholipase Dalpha in freezing-induced lipid changes in *Arabidopsis*. J. Biol. Chem. 277,31994-32002.

Wildermuth, M. C., Dewdney, J., Wu, G. and Ausubel, M. S. (2001) Isochorismate synthase is required to synthesize salicylic acid for plant defence. Nature 414, 562-571.

Yaeno, T., Matsuda, O. and Iba K. (2004) Role of chloroplast trienoic fatty acids in plant disease defense responses. Plant J. 40, 931-941.

Zhang, W., Wang, C., Qin, C., Wood, T., Olafsdottir, G., Welti, R. and Wang, X. (2003) The oleate-stimulated phospholipase D, PLD, and phosphatidic aqid decrease H2O2-induced cell death in *Arabidopsis*. Plant Cell 15, 2285-2295.

The invention claimed is:

1. A method for enhancing resistance of a plant to a pathogen, the method comprising: inducing increased levels of glycerol-3-phosphate in the plant by overexpressing glycerol-3-phosphate dehydrogenase using a transgene GLY1 from a plant; and selecting a transgenic plant for enhanced resistance to the pathogen.

2. A method for enhancing resistance of a plant to a pathogen, the method comprising: inducing increased levels of glycerol-3-phosphate in an *Arabidopsis* plant by overexpressing glycerol-3-phosphate dehydrogenase using a transgene GLY1 from a plant; and selecting a transgenic plant for enhanced resistance to the pathogen.

3. A method for enhancing resistance to of a plant to a pathogen, the method comprising: inducing increased levels of glycerol-3-phosphate in an *Arabidopsis* plant by overexpressing glycerol-3-phosphate dehydrogenase using a transgene GLY1 from a plant; and
  selecting the transgenic plant for enhanced resistance to necrotrophic and/or hemibiotrophic pathogens.

4. A method for enhancing the resistance to necrotrophic and/or hemibiotrophic pathogens, said method comprising:
  inducing overexpression of glycerol-3-phosphate dehydrogenase using an expression vector in an *Arabidopsis* plant using a transgene GLY1 from a plant which encodes the glycerol-3-phosphate dehydrogenase; and
  selecting the transgenic plant for enhanced resistance to necrotrophic and/or hemibiotrophic pathogens.

5. A method for enhancing resistance of a plant to a pathogen, the method comprising:
  inducing overexpression of a plant glycerol-3-phosphate dehydrogenase using an expression vector for expressing in the plant a gene that encodes the plant glycerol-3-phosphate dehydrogenase; and
  selecting a transgenic plant for enhanced resistance to the pathogen.

6. The method of claim 5, wherein the gene is a transgene GLY1.

7. The method of claim 5, wherein the pathogen is a necrotrophic and/or hemibiotrophic pathogen.

8. The method of claim 5, wherein the pathogen is *C. higginsianum*.

9. The method of claim 8, wherein the plant is an *Arabidopsis* plant.

10. The method of claim 5, wherein the plant is an *Arabidopsis* plant.

\* \* \* \* \*